US007825098B2

(12) United States Patent
Kahn et al.

(10) Patent No.: US 7,825,098 B2
(45) Date of Patent: Nov. 2, 2010

(54) METHODS AND COMPOSITIONS FOR MODULATING NECDIN FUNCTION

(75) Inventors: C. Ronald Kahn, West Newton, MA (US); Yu-Hua Tseng, Newton, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 745 days.

(21) Appl. No.: 11/397,514

(22) Filed: Apr. 4, 2006

(65) Prior Publication Data

US 2006/0223104 A1 Oct. 5, 2006

Related U.S. Application Data

(60) Provisional application No. 60/668,218, filed on Apr. 4, 2005.

(51) Int. Cl.
*A01N 43/04* (2006.01)
*A61K 31/70* (2006.01)
*C12Q 1/68* (2006.01)
*C12N 5/02* (2006.01)
*C12N 5/04* (2006.01)

(52) U.S. Cl. .......................... 514/44; 435/6; 435/91.1; 435/325; 435/375

(58) Field of Classification Search ................ 536/23.1, 536/24.3, 24.33, 24.5; 514/44
See application file for complete search history.

(56) References Cited

FOREIGN PATENT DOCUMENTS

WO WO 03/026576 4/2003

OTHER PUBLICATIONS

Lu et al. (2005) "Delivering siRNA in vivo for functional genomics and novel therapies" in RNA Interference Technology, Appasaini, ed. (Cambridge University Press: Cambridge, UK) p. 303-307.*
Samarsky et al. (2005) "RNAi in drug development: Practical considerations" in RNA Interference Technology Appasaini, ed. (Cambridge University Press: Cambridge, UK) p. 384-395.*
Teng et al. (Nature Cell Biology, 2005 vol. 7:601-611).*
Boeuf et al., "Differential gene expression in white and brown preadipocytes," Physiol. Genomics 7:15-26 (2001).

* cited by examiner

*Primary Examiner*—Sean McGarry
*Assistant Examiner*—Terra Cotta Gibbs
(74) *Attorney, Agent, or Firm*—Fish & Richardson P.C.

(57) ABSTRACT

Described herein are methods for identifying and using inhibitors of Necdin function to promote brown adipose tissue (BAT) differentiation, thereby treating obesity.

18 Claims, 17 Drawing Sheets

| | Up progression | |
|---|---|---|
| Probe set name | Gene name (symbol) | $q_{up}$ |
| 101975_at | delta-like 1 homolog (Drosophila) (Dlk1) | 0.004 |
| 100046_at | methylenetetrahydrofolate dehydrogenase (NADP+ dependent) 2 (Mthfd2) | 0.030 |
| 93866_s_at | matrix gamma-carboxyglutamate (gla) protein (Mglap) | 0.025 |
| 101900_at | cyclin-dependent kinase inhibitor 2B (p15, inhibits CDK4) (Cdkn2b) | 0.026 |
| 98531_g_at | growth arrest specific 5 (Gas5) | 0.004 |
| 96717_at | DEAD (Asp-Glu-Ala-Asp) box polypeptide 47 (Ddx47) | 0.014 |
| 102044_at | WNT1 inducible signaling pathway protein 1 (Wisp1) | 0.026 |
| 95529_at | drebrin-like (Dbnl) | 0.004 |
| 94367_at | uridine-cytidine kinase 2 (Uck2) | 0.006 |
| 160857_at | ephrin B2 (Efnb2) | 0.004 |
| 104048_at | cysteinyl-tRNA synthetase (Cars) | 0.030 |
| 94238_at | RIKEN cDNA 2310046G15 gene (2310046G15Rik) | 0.008 |
| 161067_at | tribbles homolog 3 (Trib3) | 0.004 |
| 93383_at | procollagen, type VII, alpha 1 (Col7a1) | 0.010 |
| 100127_at | cellular retinoic acid binding protein II (Crabp2) | 0.004 |
| 92323_at | mitogen-activated protein kinase 12 (Mapk12) | 0.004 |
| 100600_at | CD24a antigen (Cd24a) | 0.004 |
| 97500_g_at | four and a half LIM domains 1 (Fhl1) | 0.004 |
| 104449_at | glycine receptor, beta subunit (Glrb) | 0.018 |
| 96272_at | protein tyrosine phosphatase, receptor type, F (Ptprf) | 0.013 |
| 98862_at | wingless related MMTV integration site 10a (Wnt10a) | 0.018 |
| 101059_at | necdin (Ndn) | 0.004 |
| 97994_at | transcription factor 7, T-cell specific (Tcf7) | 0.004 |
| 104509_at | cholesterol 25-hydroxylase (Ch25h) | 0.004 |
| 96747_at | ras homolog gene family, member U (Rhou) | 0.004 |
| 94815_at | 2,3-bisphosphoglycerate mutase (Bpgm) | 0.004 |
| 97733_at | adenosine A2b receptor (Adora2b) | 0.026 |
| 97520_s_at | neuronatin (Nnat) | 0.014 |
| 160905_s_at | RIKEN cDNA A030009H04 gene (A030009H04Rik) | 0.004 |
| 161028_at | bone morphogenetic protein 6 (Bmp6) | 0.024 |
| 104232_at | gap junction membrane channel protein beta 3 (Gjb3) | 0.012 |
| 162011_f_at | ras homolog gene family, member U (Rhou) | 0.012 |
| 94776_f_at | killer cell lectin-like receptor, subfamily A, member 4 (Klra4) | 0.005 |

FIG. 2
(PAGE 1 OF 3)

| \multicolumn{3}{|c|}{Down progression} | | |
|---|---|---|
| Probe set name | Gene name (symbol) | qdown |
| 93503_at | secreted frizzled-related sequence protein 2 (Sfrp2) | <0.001 |
| 95493_at | procollagen, type VI, alpha 1 (Col6a1) | 0.003 |
| 101110_at | procollagen, type VI, alpha 3 (Col6a3) | <0.001 |
| 99586_at | cystatin C (Cst3) | 0.003 |
| 93077_s_at | lymphocyte antigen 6 complex, locus C (Ly6c) | 0.003 |
| 95516_at | RAB9, member RAS oncogene family (Rab9) | < 0.001 |
| 100064_f_at | gap junction membrane channel protein alpha 1 (Gja1) | 0.004 |
| 99552_at | snail homolog 2 (Drosophila) (Snai2) | 0.007 |
| 95016_at | neuropilin (Nrp) | < 0.001 |
| 101039_at | procollagen, type IV, alpha 2 (Col4a2) | 0.003 |
| 94338_g_at | growth arrest specific 2 (Gas2) | < 0.001 |
| 162459_f_at | procollagen, type VI, alpha 1 (Col6a1) | 0.002 |
| 97942_g_at | calpain 6 (Capn6) | < 0.001 |
| 97943_at | calpain 6 (Capn6) | 0.002 |
| 94345_at | interleukin 6 signal transducer (Il6st) | 0.002 |
| 92877_at | transforming growth factor, beta induced (Tgfbi) | 0.003 |
| 96662_at | phosphatidic acid phosphatase type 2B (Ppap2b) | < 0.001 |
| 160638_at | cyclin-dependent kinase inhibitor 2C (p18, inhibits CDK4) (Cdkn2c) | < 0.001 |
| 93188_at | dickkopf homolog 3 (Xenopus laevis) (Dkk3) | < 0.001 |
| 98136_at | spermine synthase (Sms) | < 0.001 |
| 100435_at | endothelial differentiation, lysophos. acid G-prot-coupled rcptr 2 (Edg2) | 0.006 |
| 103756_at | cDNA sequence BC023829 (BC023829) | 0.003 |
| 102223_at | periplakin (Ppl) | 0.002 |
| 93728_at | transforming growth factor beta 1 induced transcript 4 (Tgfb1i4) | 0.007 |
| 104003_at | phosphorylase kinase alpha 2 (Phka2) | 0.002 |
| 93743_at | heat shock factor binding protein 1 (Hsbp1) | 0.027 |
| 93914_at | interleukin 1 receptor, type I (Il1r1) | 0.002 |
| 92555_at | transmembrane 4 superfamily member 6 (Tm4sf6) | < 0.001 |
| 93913_at | RIKEN cDNA 3110018A08 gene (3110018A08Rik) | < 0.001 |
| 95731_at | sestrin 1 (Sesn1) | 0.003 |
| 95019_at | glutathione S-transferase, theta 1 (Gstt1) | 0.007 |
| 104174_at | ectonucleotide pyrophosphatase/phosphodiesterase 1 (Enpp1) | < 0.001 |
| 162081_f_at | RIKEN cDNA 0610010E05 gene (0610010E05Rik) | 0.004 |
| 99444_at | receptor (calcitonin) activity modifying protein 2 (Ramp2) | < 0.001 |
| 104601_at | thrombomodulin (Thbd) | < 0.001 |
| 102327_at | amine oxidase, copper containing 3 (Aoc3) | 0.003 |
| 160319_at | SPARC-like 1 (mast9, hevin) (Sparcl1) | < 0.001 |

FIG. 2
(PAGE 2 OF 3)

| 92357_at | a disintegrin and metalloprotease domain 23 (Adam23) | 0.003 |
|---|---|---|
| 92722_f_at | sine oculis-related homeobox 1 homolog (Drosophila) (Six1) | < 0.001 |
| 98924_at | ADP-ribosyltransferase 3 (Art3) | < 0.001 |
| 102657_at | H2.0-like homeo box 1 (Drosophila) (Hlx) | 0.006 |
| 98960_s_at | UDP-Gal:betaGlcNAc beta 1,3-galactosyltransferase (B3galt3) | 0.006 |
| 102871_at | Eph receptor B6 (Ephb6) | 0.003 |
| 96122_at | RIKEN cDNA 2310016A09 gene (2310016A09Rik) | 0.003 |
| 100065_r_at | gap junction membrane channel protein alpha 1 (Gja1) | 0.007 |
| 97941_at | calpain 6 (Capn6) | 0.006 |
| 160530_at | growth hormone inducible transmembrane protein (Ghitm) | 0.022 |
| 100697_at | paired box gene 3 (Pax3) | 0.007 |
| 104519_at | inter-alpha trypsin inhibitor, heavy chain 2 (Itih2) | 0.012 |
| 161173_f_at | interferon activated gene 202B (Ifi202b) | 0.018 |
| 101991_at | flavin containing monooxygenase 1 (Fmo1) | 0.003 |
| 103484_at | popeye domain containing 3 (Popdc3) | 0.003 |
| 100567_at | fatty acid binding protein 4, adipocyte (Fabp4) | 0.007 |
| 103493_at | neuromedin B (Nmb) | 0.017 |

FIG. 2

(PAGE 3 OF 3)

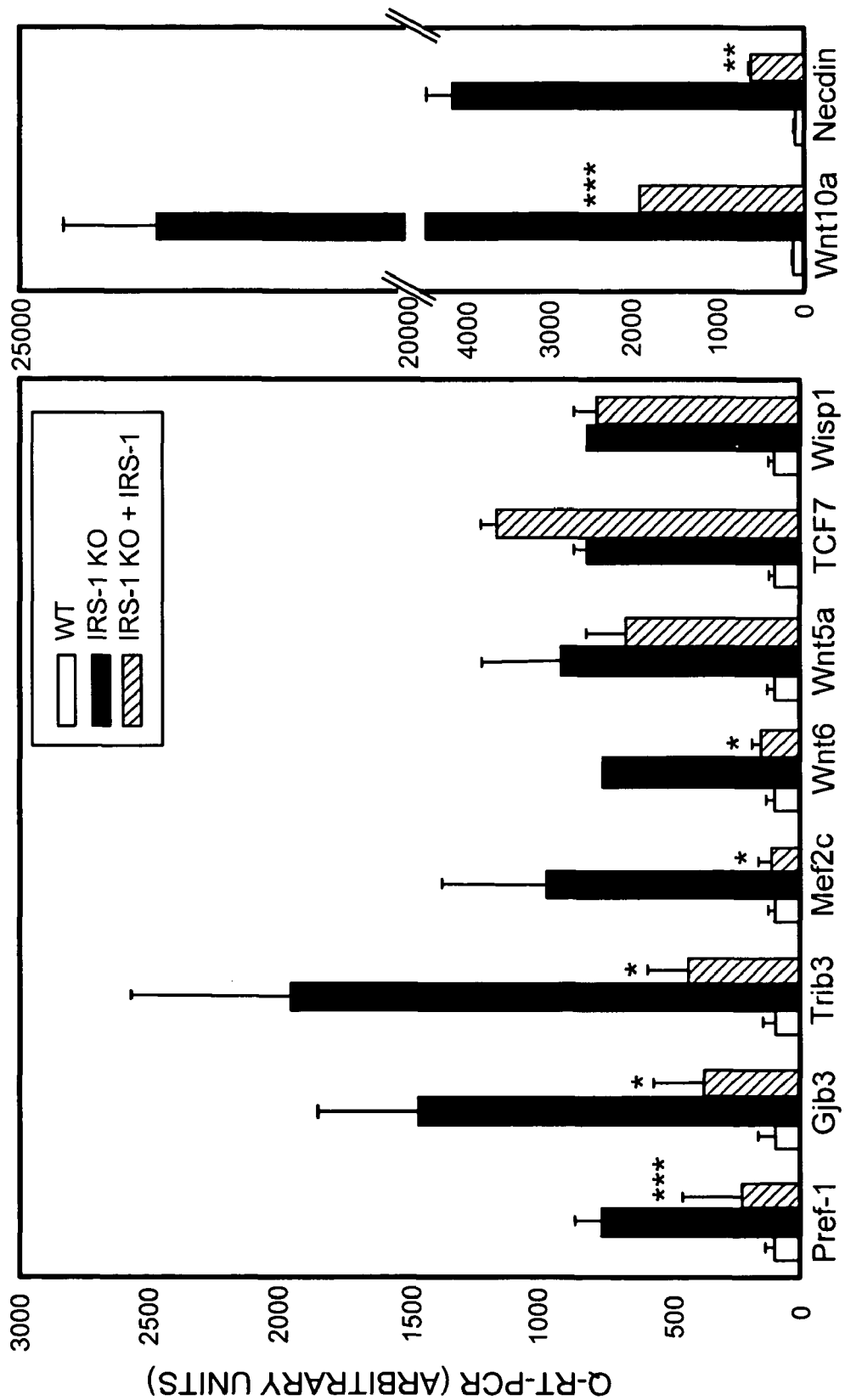

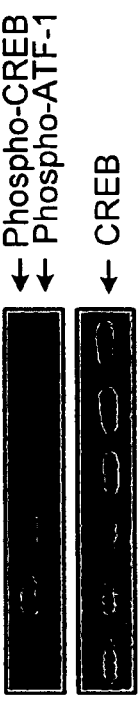
FIG. 6C
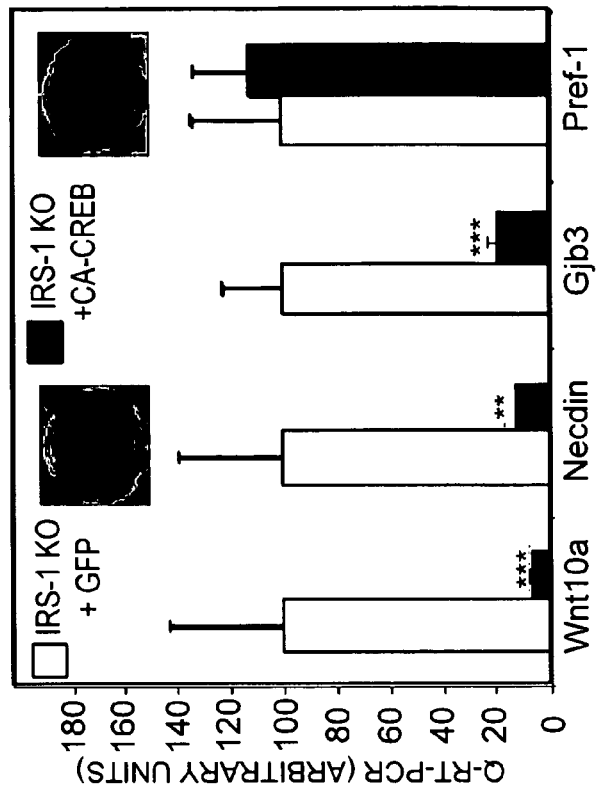
FIG. 6A
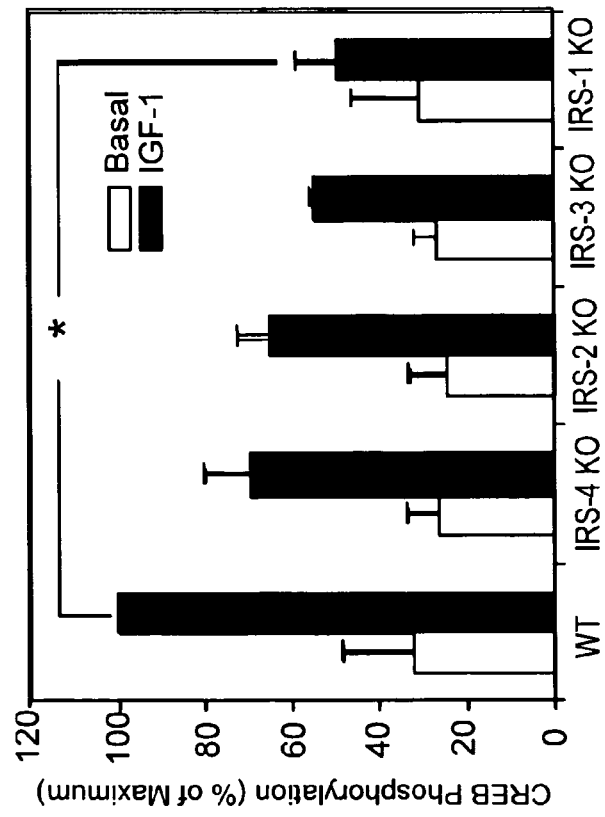
FIG. 6D
FIG. 6B

```
1   MSEQSKDLSD PNFAAEAPNS EVHSSPGVSE GVPPSATLAE PQSPPLGPTA APQAAPPPQA
61  PNDEGDPKAL QQAAEEGRAH QAPSAAQPGP APPAPAQLVQ KAHELMWYVL VKDQKKMIIW
121 FPDMVKDVIG SYKKWCRSIL RRTSLILARV FGLHLRLTSL HTMEFALVKA LEPEELDRVA
181 LSNRMPMTGL LLMILSLIYV KGRGARESAV WNVLRILGLR PWKKHSTFGD VRKLITEEFV
241 QMNYLKYQRV PYVEPPEYEF FWGSRASREI TKMQIMEFLA RVFKKDPQAW PSRYREALEE
301 ARALREANPT AHYPRSSVSE D (SEQ ID NO:1)
```

FIG. 10

```
   1 aagcttaaga gtcctgttgg agggactggt gtggtaatgg ctctgccaaa agtgttatgt
  61 gcgtgcaaac ccaaagagag aaagcacaga aaacctttca acatcaacct gcttgaggaa
 121 aaataaagtg ggaaaagata catactcaca gtgaggactc tagacatgtc aagacaattt
 181 ttaaatatgc tttggcttc gagtggcaat aactagattc aagacagcat atttaagaag
 241 ctgctgatga gaagaaaccc gggaaagct gaaggaccac atcagcccag accaaggatg
 301 ctgaagcagc attaagtcc ctggtttcag atgctcaggc aatgaccctt tttttcatgg
 361 agagcctgta ggagtgacag tttgtcttt gcccactggg aatctgtttt ccatacctgg
 421 aaaacagggt tacctatgtt tccctgcta cccttggtc atctcagaga cactaccaga
 481 tattaccat gggacctatt tttttttaa atctcaggaa agacttgggt gtggcttcca
 541 acgtggagga ctcagtagct tcagagaggg tcctgagaga aggtgaattg aagaatgagg
 601 gtgctgggca aagggaaaag acattatcat gcaagttgt gctaaaagat atagcaatcc
 661 ttctgctatg gactaagtat ggaaaaaaat aaaatggaat caaagttacc caaagaatt
 721 gtaaaaccca atttatgccc gttaaagcat taatgatgct ctaagtccac tgcctactta
 781 aaaagttcat agttcacatg ggtttgatag gaaattacgt ttaacgacac actgcatttc
 841 cccttttctt atagcctatc tgatttggta gggagtcgat catttttat tggaatttct
 901 caggattcca acctcagaca tccactttac agtttacaca tttctttgga caagcccgac
 961 tgttcctctc actggttcgc ataaagctca tgtttacaaa gccgcccaga cctttctctg
1021 ggactctcat atttaactta attctggata taccaggta agcgtttccc aagaaacttg
1081 acccaacat cccaaaaact taggtatct ttccctaaa ctggcccct ctccagtacg
1141 catccatctc acttctctcc tgccctagat cttctcagcc caaacaggaa acccgggat
1201 cgctctccca gcaggtgaag cctcgccatg gaccctcccc gtcgggccc gcgctgccc
1261 cgcccgcccc cagccgctgg ccaaggccgc ggtcgcgcag gcgcgcgcg gcgtccccgc
1321 gccgcccgc cctgcccgtc gctgcccgcg gcgggaag gcgccgcg cagcaacgcg cacttcctct
1381 ccaggaatcc gcggagggag cgcaggctcg aagagctcct ggacgcagag gccctgccct
1441 tgccagacgg cgcagacatg (SEQ ID NO:2)
```

METHODS AND COMPOSITIONS FOR MODULATING NECDIN FUNCTION

CLAIM OF PRIORITY

This application claims the benefit under 35 U.S.C §119(e) of U.S. Provisional Patent Application Ser. No. 60/668,218, filed on Apr. 4, 2005, the entire contents of which are hereby incorporated by reference.

FEDERALLY SPONSORED RESEARCH OR DEVELOPMENT

This invention was made with Government support under grants DK33201, DK60837, DK101183, and DK63696 awarded by the National Institutes of Health. The U.S. Government has certain rights in this invention.

TECHNICAL FIELD

This invention relates to methods of treating obesity by modulating Necdin function.

BACKGROUND

Adipogenesis is a complex process that is highly regulated by positive and negative stimuli, including a variety of hormones and nutritional signals (Gregoire et al., *Physiol. Rev.,* 78:783-809 (1998); Cowherd et al., *Semin. Cell Dev. Biol.,* 10:3-10 (1999); Rangwala et al., *Annu. Rev. Nutr.,* 20:535-559 (2000); Rosen et al., *Genes Dev.,* 14:1293-1307 (2000); Gregoire, *Exp. Biol. Med.* (*Maywood*), 226:997-1002 (2001); Koutnikova et al., *Ann. Med.,* 33:556-561 (2001); Camp et al., *Trends Mol. Med.,* 8:442-447 (2002); MacDougald et al., *Trends Endocrinol. Metab.,* 13:5-11 (2002)). At the cellular and molecular levels, parts of the program of adipogenesis has been relatively well delineated. Preconfluent preadipocytes undergo proliferation and growth arrest, but when triggered by proper stimuli, undergo clonal expansion leading to a second growth arrest followed by terminal differentiation (Gregoire et al., *Physiol. Rev.,* 78:783-809 (1998); Cowherd et al., *Semin. Cell Dev. Biol.,* 10:3-10 (1999)). The latter part of this process is under a complex series of transcriptional controls involving CCAAT/enhancer-binding protein (C/EBP) β, δ, α, peroxisome proliferator-activated receptor (PPAR)γ, the signal transducers and activators of transcription (STAT)-1, -3, -5, and others (Rosen et al., *Genes Dev.,* 14:1293-1307 (2000); Aubert et al., *Cell. Mol. Life Sci.,* 56:538-542 (1999); Stephens et al., *J. Biol. Chem.,* 271: 10441-10444 (1996); Harp et al., *Biochem. Biophys. Res. Commun.,* 281:907-912 (2001)). This precedes the synthesis of proteins characteristic of a fully differentiated phenotype, such as fatty acid synthase (FAS) and glucose transporter-4 (Glut-4, official gene symbol is Slc2a4). More recently, PPARγ coactivator-1 (known as PGC-1α or Ppargc1a) has been identified as a potential unique regulator leading to brown fat differentiation, involving the induction of uncoupling protein (UCP)-1 expression (Puigserver et al., *Cell,* 92:829-839 (1998)).

Less is known about the events prior to the initiation of this transcriptional cascade during which preadipocytes are released from suppressions and become committed to terminal differentiation (Gregoire et al., *Physiol. Rev.,* 78:783-809 (1998); MacDougald et al., *Trends Endocrinol. Metab.,* 13:5-11 (2002)). Some of the known inhibitors of the preadipocyte-adipocyte transition for white fat include the Wnt family of proteins (Ross et al., *Science,* 289:950-953 (2000)), preadipocyte factor-1 (Pref-1, also known as Dlk1) (Smas et al., *Cell,* 73:725-734 (1993)), Gata3 (Tong et al., *Science,* 290: 134-138 (2000)), and the retinoblastoma (pRb) family of proteins (Chen et al., *Genes. Dev.,* 10:2794-2804 (1996)). Very little is known about whether similar mechanisms play a role in brown adipocyte differentiation, or which factors and mechanisms regulate the production and function of these inhibitors.

Both insulin and IGF-1 have been shown to exert effects on adipocyte differentiation in vivo and in vitro (Gregoire et al., *Physiol. Rev.,* 78:783-809 (1998); MacDougald et al., *Trends Endocrinol. Metab.,* 13:5-11 (2002)). These factors utilize a complex signalling pathway to exert their pleiotropic biological effects involving activation of their respective cell surface receptors and phosphorylation of several intracellular insulin/ IGF-1 receptor substrates (IRS). Brown preadipocytes lacking insulin receptors fail to differentiate (Entingh et al., *J. Biol. Chem.,* 278:33377-33383 (2003)), and cells lacking IRS proteins show a range of differential defects, from normal differentiation in IRS-4 knockout (KO) cells to severely impaired adipogenesis in IRS-1 KO preadipocytes (Tseng et al., *Mol. Cell. Biol.,* 24:1918-1929 (2004)).

Necdin is a growth suppressor that is expressed in virtually all postinitotic neurons in the brain. See, e.g., OMIM entry No. *602117. The necdin polypeptide sequence is given at Genbank Acc. No. Q99608. The *homo sapiens* necdin gene, promoter and 5'UTR region are given at Genbank Acc. No. AF000113.1.

SUMMARY

Insulin and IGF-1 promote adipocyte differentiation via complex and overlapping signalling networks. The present inventors used microarray analysis of brown preadipocytes derived from wild-type and insulin receptor substrate (IRS) knockout (KO) animals, which exhibited progressively impaired differentiation, to define a set of genes that predict adipogenic potential in these cells. 374 genes/ESTs were identified whose expression in preadipocytes correlated with their ultimate ability to differentiate. Many of these genes were related to early adipogenic events, including genes involved in extracellular matrix, cytoskeletal organization, growth arrest, post-mitotic clonal expansion, and inhibitors of adipogenesis, including preadipocyte factor-1 and multiple members of the Wnt-signalling pathway. Reconstitution of IRS-1 KO cells with IRS-1 reversed these changes and restored the ability to differentiate. Several of these genes showed concordant changes in brown adipose tissue in vivo. Necdin was markedly increased in IRS-1 KO cells that could not differentiate, and knockdown of necdin restored brown adipogenesis with down-regulation of Pref-1 and Wnt10a expression. The results described herein demonstrate a necdin-E2F4 interaction repressing PPARγ transcription. IRS proteins regulated necdin via a CREB dependent pathway, defining a signalling network involved in brown preadipocyte determination.

Thus, the invention includes methods of promoting brown adipocyte tissue (BAT) differentiation, by contacting a preadipocyte or adipocyte cell or tissue with an inhibitor of Necdin function in an amount sufficient to promote BAT differentiation. In some embodiments, the cell or tissue comprises a brown preadipocyte, a white preadipocyte or white adipocyte.

In some embodiments, the cell or tissue is in a living subject, e.g., an obese human subject. In some embodiments, the cell or tissue is in culture; in these embodiments, the methods can include implanting the cells into a subject, e.g., an obese human subject. In some embodiments, the cells express necdin.

In some embodiments, the methods also include contacting the cell with another agent selected from the group consisting of bone morphogenetic protein 2 (BMP-2), bone morphogenetic protein 4 (BMP-4), bone morphogenetic protein 5 (BMP-5), bone morphogenetic protein 6 (BMP-6), or bone morphogenetic protein 7 (BMP-7), bone morphogenetic protein 1 (BMP-1), bone morphogenetic protein 3 (BMP-3), peroxisome proliferator-activated receptor-γ (PPARγ), Retinoid X receptor, alpha (RxRa), insulin, T3, a thiazolidinedione (TZD) (e.g., rosiglitazone or pioglitazone), vitamin A, retinoic acid, insulin, glucocorticoid or agonist thereof, Wingless-related MMTV integration site (Wnt), insulin-like growth factor (IGF), epidermal growth factor (EGF), fibroblast growth factor (FGF), transforming growth factor alpha (TGFα), TGFβ, tumor necrosis factor alpha (TNFα), Macrophage colony stimulating factor (MCSF), vascular endothelial growth factor (VEGF) and Platelet Derived Growth Factor (PDGF).

Also provided herein are methods for identifying an agent that promotes BAT differentiation, by identifying an agent that decreases, e.g., significantly decreases, expression, levels or activity of Necdin.

In some embodiments, the methods include providing a cell that can express Necdin; contacting the cell with a test compound; and evaluating the effect of the test compound on the expression, levels or activity of Necdin. A test compound that increases expression, levels or activity of Necdin is an agent that promotes BAT differentiation.

In some embodiments, the methods also include correlating the ability of the agent to increase expression, levels or activity of Necdin, with the ability to promote BAT differentiation.

In another aspect, the invention provides methods for identifying a candidate therapeutic agent for the treatment of obesity. The methods include providing an animal model of obesity; administering an agent that promotes BAT differentiation to the animal model; and evaluating the effect of the agent on obesity in the animal model. An agent that decreases obesity in the animal model is a candidate therapeutic agent for the treatment of obesity. In some embodiments, the methods also include administering to the animal a second agent selected from the group consisting of bone morphogenetic protein 2 (BMP-2), bone morphogenetic protein 4 (BMP-4), bone morphogenetic protein 5 (BMP-5), bone morphogenetic protein 6 (BMP-6), or bone morphogenetic protein 7 (BMP-7), bone morphogenetic protein 1 (BMP-1), bone morphogenetic protein 3 (BMP-3), peroxisome proliferator-activated receptor gamma (PPARγ), Retinoid X receptor, alpha (RxRa), insulin, T3, a thiazolidinedione (TZD), vitamin A, retinoic acid, insulin, glucocorticoid or agonist thereof, Wingless-related MMTV integration site (Wnt), insulin-like growth factor (IGF), epidermal growth factor (EGF), fibroblast growth factor (FGF), transforming growth factor alpha (TGFα), transforming growth factor beta (TGFβ), tumor necrosis factor alpha (TNFα), Macrophage colony stimulating factor (MCSF), vascular endothelial growth factor (VEGF) and Platelet Derived Growth Factor (PDGF).

In some embodiments, the methods further include administering the candidate therapeutic agent for the treatment of obesity to a subject in a clinical trial, and evaluating the effect of the candidate therapeutic agent on obesity in the subject.

In a further aspect, the invention includes methods for decreasing fat stores or weight in a subject, e.g., a diabetic subject, by administering to the subject a therapeutically effective amount of an inhibitor of Necdin function, e.g., a candidate therapeutic agent identified by a method described herein.

Also provided herein are methods for decreasing fat stores or weight in a subject, e.g., a diabetic subject, by identifying a subject in need of decreasing fat stores or weight, and administering to the subject a therapeutically effective amount of an inhibitor of Necdin function in an amount sufficient to promote BAT differentiation in the subject. In some embodiments, the methods also include administering to the animal a second agent selected from the group consisting of bone morphogenetic protein 2 (BMP-2), bone morphogenetic protein 4 (BMP-4), bone morphogenetic protein 5 (BMP-5), bone morphogenetic protein 6 (BMP-6), or bone morphogenetic protein 7 (BMP-7), bone morphogenetic protein 1 (BMP-1), bone morphogenetic protein 3 (BMP-3), peroxisome proliferator-activated receptor gamma (PPARγ), Retinoid X receptor, alpha (RxRa), insulin, T3, a thiazolidinedione (TZD), vitamin A, retinoic acid, insulin, glucocorticoid or agonist thereof, Wingless-related MMTV integration site (Wnt), insulin-like growth factor (IGF), epidermal growth factor (EGF), fibroblast growth factor (FGF), transforming growth factor alpha (TGFα), transforming growth factor beta (TGFβ), tumor necrosis factor alpha (TNFα), Macrophage colony stimulating factor (MCSF), vascular endothelial growth factor (VEGF) and Platelet Derived Growth Factor (PDGF).

Further, the invention provides methods for determining if a subject is at risk for weight gain or obesity. The methods include obtaining a test sample from the subject, e.g., a test sample comprising adipocytes, e.g., one or more of a brown adipocyte, a white adipocyte, a brown preadipocyte, and a white preadipocyte; evaluating the expression, protein level or activity of Necdin in the test sample; and comparing the expression, protein level or activity of Necdin in the test sample to that in a control. A decrease in the expression, protein level or activity of Necdin in the test sample relevant to the control indicates that the subject is at risk for weight gain or obesity.

In some embodiments, an inhibitor of Necdin function reduces Necdin expression, e.g., by affecting one or more of: mRNA half life, transcription, translation, protein half life, subcellular localization, or post-translational modification.

In some embodiments, the inhibitor of Necdin function is selected from the group consisting of a Necdin-specific antisense nucleic acid, aptamer, small interfering RNA (siRNA), antibody, or ribozyme.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2 lists genes that show up- or down-progression correlated with the phenotypes. 33 genes were defined as up-progressors and significantly different between IRS-1 KO cells and their WT controls and 54 genes were similarly different but were down-progressors using the criteria described herein. The $q_{up}$ or $q_{down}$ values indicate the degree of significance of the up- and down-progression, respectively, in terms of the expected false discovery rate if each gene were significant. The q-values are listed in italics if the p-value from Levene's test for the gene was <0.05, indicating that the gene may not have homogenous variances, which may limit interpretation of the gene using Bartholemew's test of homogeneity for ordered alternatives. The genes are sorted in descending order by mean expression in WT.

FIGS. 3A-E are bar graphs illustrating the results of quantitative RT-PCR analyses confirming changes in gene expression in vitro and in vivo. Total RNAs isolated from WT, IRS-1 KO and IRS-1 KO reconstituted with IRS-1 cells (3A, 3B and 3C) as well as brown (3D) and white (3E) adipose tissues from WT, IRS-1 KO and IRS-⅓ double KO (DKO) mice (n=3-5) were analysed by quantitative RT-PCR (Q-RT-PCR). Data are presented as mean±SEM. Significance was determined by unpaired, unequal t test. Expression of genes shown in panels 3A, 3B and 3C significantly differed between WT and IRS-1 KO cells. Asterisks depict statistically significant differences between IRS-1 KO and IRS-1 KO reconstituted with IRS-1 (3A, 3B and 3C) or between adipose tissues isolated from WT and KO or DKO mice (C and D) (*=P<0.05, =P <0.01, *=P<0.001).

FIGS. 6A-D illustrate the regulation of gene expression by CREB. 6A is a representative Western blot of basal and IGF-1 stimulated (10 nM, 5 minutes) Ser 133 phosphorylation of CREB in WT and different IRS KO brown preadipocytes. 6B is a bar graph of data from three independent experiments were quantitated and presented as mean±SEM. 6C is a Western blotting analysis of Ser 133 phosphorylation of CREB by 10 nM of IGF-1 [G] or 10 µM of forskolin [F] for 5 minutes in WT and IRS-1 KO brown preadipocytes. The blots were stripped and reprobed with a non-phospho-specific anti-CREB antibody to normalize for variation in loading and transfer of proteins. 6D is a graph of results of quantitative RT-PCR analysis for Wnt10a, necdin, GJB-3 and Pref-1 using total RNAs isolated form preadipocytes of IRS-1 KO stably expressing a constitutively active form of CREB (CA-CREB) or the control green florescent protein (GFP). Inserts show Oil Red O staining of these cells at day 6 of differentiation. Data are presented as mean±SEM. Significance was determined by unpaired, unequal t test with *=P<0.05, =P<0.01, *=P<0.001.

FIGS. 10 and 11 are the sequences of human necdin protein (10, SEQ ID NO:1) and gene (11, SEQ ID NO:2). The 5'UTR is bases 1299-1460.

DETAILED DESCRIPTION

At least in part, the invention described herein is based on the discovery that necdin is involved in adipocyte differentiation. Specifically, elevated levels of necdin inhibit brown adipocyte (BAT) differentiation. Necdin is thus a therapeutic, diagnostic and drug discovery target for adipose-related disorders, such as obesity and related disorders such as diabetes, insulin resistance, hyperglycemia, hyperlipidemia, and hypercholesterolemia.

Figure 7:
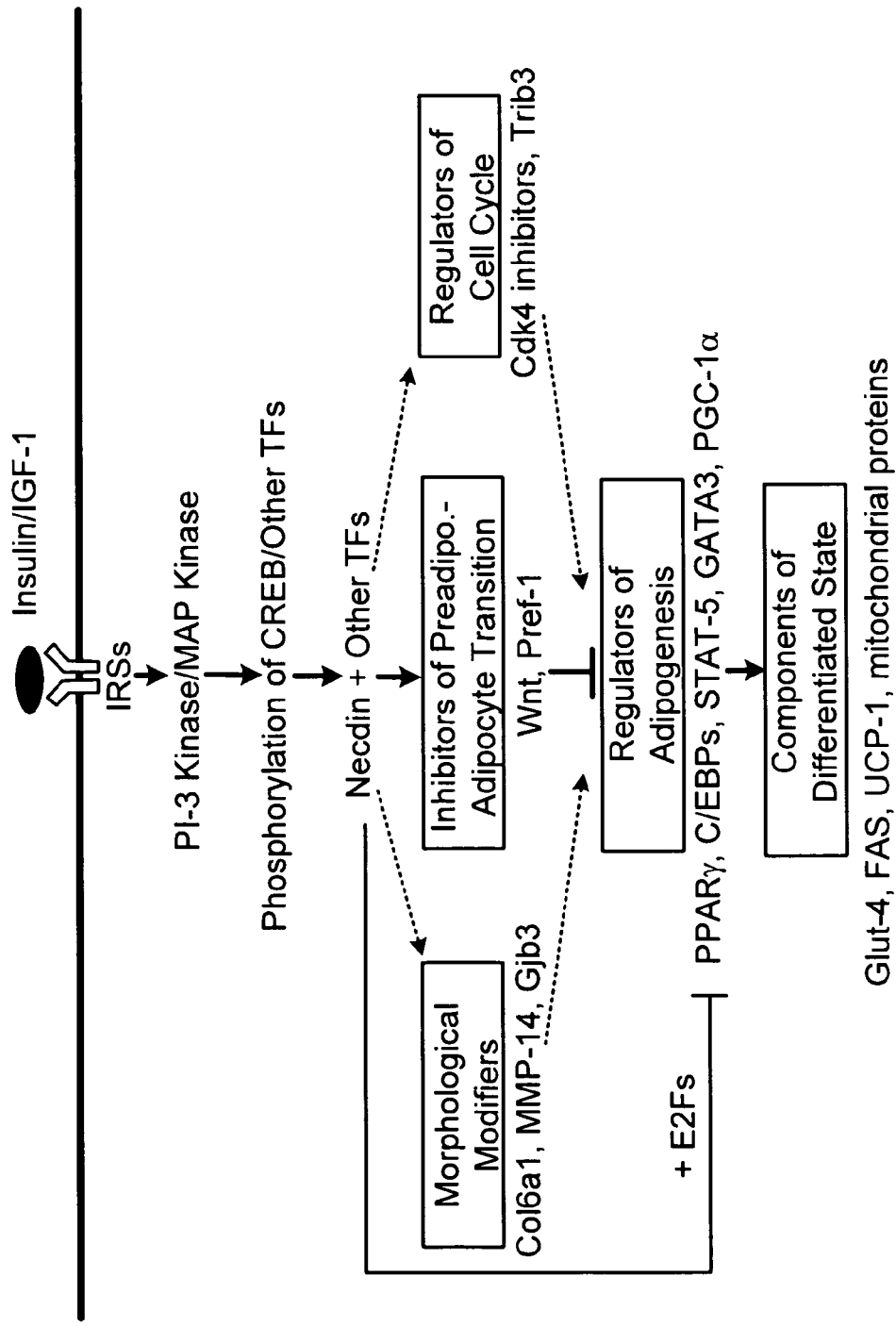
FIG. 7 is a proposed model of regulation of brown adipogenesis by the insulin/IGF-1/IRS pathway. In brown preadipocytes, activation of the cell surface receptors of insulin or IGF-1 results in phosphorylation of the IRS proteins and leads to activation of the PI 3-kinase and the MAP kinase pathways. These in turn modulate the activity of transcription factors, such as CREB and others, via a phosphorylation-dependent mechanism. One potential function of these signalling cascades is to suppress expression of necdin, which acts upstream to other inhibitors of preadipocyte-adipocyte transition, such as Pref-1 and Wnt pathways. Necdin also represses PPARγ promoter activity via interaction with E2Fs. The insulin/IGF-1/IRS pathway also regulates expression of several genes involved in other early adipogenic events, such as morphological modifiers and regulators of cell cycle. These then trigger the expression and activation of a complex series of adipogenic transcription factors, involving C/EBPs, PPARγ and others, leading to termination differentiation. Dash lines depict either positive or negative regulation.

Dramatic changes in gene expression occur as preadipocytes differentiate into adipocytes (Rangwala et al., *Annu. Rev. Nutr.*, 20:535-559 (2000); Rosen et al., *Genes Dev.*, 14:1293-1307 (2000)), however, the factors that influence preadipocyte determination and the very early signals that regulate these factors remain poorly understood. In this study, we demonstrate that the insulin/IGF-1/IRS pathway plays an important role in regulation of genes involved in multiple early adipogenic events in brown preadipocytes and that this involves a highly coordinated series of gene regulatory events that can be identified even in the preadipocyte. Based on the present and published data (Fasshauer et al., *Mol. Cell. Biol.*, 21:319-329 (2001); Tseng et al., *J. Biol. Chem.*, 277:31601-31611 (2002); Entingh et al., *J. Biol. Chem.*, 278:33377-33383 (2003); Tseng et al., *Mol. Cell. Biol.*, 24:1918-1929 (2004)), a theoretical model, not meant to be limiting, for the role of the insulin/IGF-1/IRS pathway in regulation of brown adipogenesis is illustrated in FIG. 7.

In brown preadipocytes, activation of the cell surface receptors of insulin or IGF-1 results in phosphorylation of the IRS proteins, leading to activation of the PI3-kinase and the Ras/MAP kinase pathways. Both of these pathways modulate the activities of several transcription factors and thereby regulate gene expression involved in adipogenesis. The present study indicates that CREB and necdin may serve as potential links between these upstream signalling events and downstream gene expression. In particular, necdin appears to play a coordinated role in mediating the CREB effect on downstream gene expression. Multiple genes are regulated by these pathways to impact on early adipogenic events. These include genes involved in extracellular matrix and cytoskeletal organization, growth arrest, post-mitotic clonal expansion, and inhibitors of adipogenesis. These lead to the initiation of a transcriptional cascade involving C/EBPs, PPARγ, and PGC-1α, which program the final changes required for full differentiation of the brown adipocytes with expression of Glut-4, FAS, UCP-1 and mitochondrial proteins involved in oxidative phosphorylation.

Taking advantage of gene expression profiling and brown preadipocytes which lack IRS-1, -2, -3, or -4 and show varying degrees of defects in differentiation, 276 genes/ESTs have been identified that differ in expression between WT and IRS-1 deficient brown preadipocytes (the most defective in differentiation); 82 of these have expression patterns that parallel the defect in differentiation in all five genotypes. Most importantly, these changes in gene expression can already be detected in the undifferentiated fibroblastic preadipocyte indicating that the alterations in the insulin/IGF signalling pathway have affected preadipocyte determination. These differentially expressed genes include many known to be involved in early adipogenesis, such as Pref-1, components of the Wnt signalling pathway and multiple proteins of the cytoskeleton and extracellular matrix, as well as genes not previously linked to adipogenesis, such as necdin.

One of the challenging issues in studies of expression profiling is to identify the transcription factors that drive the coordinated changes in gene expression observed in the microarray studies. Using bioinformatic and biological approaches, CREB and necdin have been identified as two potential links between the upstream signalling events and the changes in gene expression.

CREB activation by insulin and other agents is required for 3T3-L1 differentiation (Reusch et al., *Mol. Cell. Biol.*, 20:1008-1020 (2000); Klemm et al., *J. Biol. Chem.*, 276:28430-28435 (2001)). In brown preadipocytes, the level of IGF-1-stimulated CREB phosphorylation was progressively decreased in the IRS KO cells with increasing defects in differentiation. Overexpression of the constitutively active CREB in IRS-1 KO cells reversed many of these changes in gene expression, but alone only partially restore the defect in differentiation. Similarly, overexpression of a dominant negative CREB in WT cells did not completely block brown adipogenesis, suggesting that CREB activation in brown preadipocytes is essential for some aspects of gene expression, but is not sufficient to initiate the whole adipogenic program.

Expression profiling of cells with varying adipogenic potential has identified important new players in the regulation of adipogenesis, and one of these is necdin, a protein that is functionally similar to the pRb protein. Necdin is highly up-regulated in preadipocytes that have a defect in differentiation, suggesting that necdin may function as a negative regulator in the early stages of brown adipocyte differentiation. During the normal adipogenic process, down-regulation of necdin expression by insulin or IGF-1 in the preadipocyte appears to be essential for brown adipogenesis. The results described herein indicate that necdin acts upstream to other inhibitors of preadipocyte-adipocyte transition, such as Pref-1 and Wnt10a, and knocking-down necdin expression results in decrease in the overexpression of these genes and restoration of differentiation.

At the molecular level, necdin may exert this regulatory effect via interaction with the E2F family of transcription factors acting on PPARγ gene transcription. Thus, in cells transfected with E2F4 alone, PPARγ promoter activity is increased, while co-expression of necdin with E2F4 suppresses this activity. E2Fs have been previously shown to play a role in white adipogenesis (Fajas et al., *Dev. Cell*, 3:39-49 (2002); Landsberg et al., *Proc. Natl. Acad. Sci. USA*, 100:2456-2461 (2003)). The patterns of E2F1 and E2F4 protein expression during brown adipocyte differentiation, however, are quite distinct from those observed in white adipocyte differentiation. In 3T3-L1 cells, E2F4 is increased during differentiation (Fajas et al., *Dev. Cell*, 3:39-49 (2002)), whereas in normal brown adipogenesis, expression of E2F4 rapidly declines as differentiation proceeds. However, in cells with high levels of necdin which differentiate poorly, such as IRS-1 KO and IRS-3 KO cells, the level of E2F4 protein remains high. This suggests that like pRb protein that binds and stabilizes E2F1 by protecting it from ubiquitination (Martelli et al., *Proc. Natl. Acad. Sci. USA*, 96:2858-2863 (1999)), necdin may stabilize E2F4 protein during late stage of differentiation.

The complete role of E2F4 on adipogenesis is not fully understood. While E2F4 is able to induce PPARγ promoter activity in both white (Fajas et al., *Dev. Cell*, 3:39-49 (2002)) and brown adipogenesis (this study), mouse embryonic fibroblasts (MEFs) lacking E2F4 can undergo spontaneous differentiation toward fat (Landsberg et al., *Proc. Natl. Acad. Sci. USA*, 100:2456-2461 (2003)). As described herein, overexpression of E2F4 in IRS-1 KO brown preadipocytes could partially restore differentiation, suggesting a stimulatory effect of E2F4 on brown adipogenesis. The findings of increased adipogenesis in both MEFs devoid of E2F4 and IRS-1 KO brown preadipocytes with increased E2F4 expression may suggest a differential effect of E2F4 in white vs. brown adipogenesis. Alternatively, the effect of E2F4 on adipocyte differentiation may be dependent on the stage of cells, since MEFs resemble mesenchymal stem cells, whereas the cells used in this study are already committed preadipocytes; or simply the effect of E2F4 on differentiation is modulated by many other factors that differ in these two cell types.

While the exact function of necdin remains unclear, necdin appears to play an important role in differentiation. Necdin was initially isolated from embryonal carcinoma cells induced to undergo neuronal differentiation and is highly expressed in most of the terminally differentiated neurons (Goldstone, *Trends Endocrinol. Metab.*, 15:12-20 (2004); Taniura et al., *J. Biol. Chem.*, 273:720-728 (1998)). However, expression of necdin is not restricted to neuronal tissues (Yang et al., *Nat. Genet.*, 19:25-31 (1998)). Boeuf et al. have shown that necdin is one of the genes that is differentially expressed between white and brown preadipocytes (Boeuf et al., *Physiol. Genomics*, 7:15-25 (2001)). Recently, necdin has been found to interact with transcription factor Msx2 to specify myogenic differentiation (Brunelli et al., *Circ. Res.*, 94:1571-1578 (2004); Kuwajima et al., *J. Biol. Chem.*, 279: 40484-40493 (2004)). Interestingly, the human necdin gene maps to chromosome 15q11.2-q12, a region deleted in Prader-Willi syndrome (PWS). PWS is a neurodevelopmental disorder characterized by global developmental delay, mental retardation, feeding problems, hypogonadism, hyperphasia and gross obesity (Goldstone, *Trends Endocrinol. Metab.*, 15:12-20 (2004)). The role of these pathways in more common forms of obesity and diabetes in humans remains to be determined, however, low IRS-1 expression in fat has been identified as a marker of insulin resistance, a risk for type 2 diabetes and is associated with evidence of early vascular complications (Jansson et al., *FASEB J*, 17:1434-1440 (2003)). Thus, genes that are altered in expression in the IRS-1 KO preadipocytes provide not only additional cellular markers but also potential molecular targets for drug development to treat obesity, diabetes and its complications.

Adipose Tissue

The most commonly known fat cells are white fat cells, also known as white adipose tissue (WAT) cells, which have a thin ring of cytoplasm surrounding a lipid or fat droplet. WAT is found underneath the skin and provides heat insulation, cushioning against shock and jarring, and energy reserves. An average lean person has roughly 20 to 40 billion WAT cells. An obese person can have up to ten times more WAT than the average lean person.

The less common fat cells are the brown fat cells, also known as brown adipose tissue (BAT) cells. Energy expenditure for thermogenesis in BAT serves either to maintain body temperature in the cold or to waste food energy. It has roles in thermal balance and energy balance, and when defective, is usually associated with obesity. BAT is typically atrophied in obese animals. The importance of BAT in overall energy homeostasis is underscored by the finding that ablation of BAT in mice results in severe obesity accompanied by insulin resistance, hyperglycemia, hyperlipidemia, and hypercholesterolemia (Lowell at al., *Nature*, 366(6457):740-742 (1993); Hamann et al., *Diabetes*, 44(11):1266-1273 (1995); Hamann et al., *Endocrinology*, 137(1):21-29 (1996)).

Adipose tissues contain a potential mitotic compartment, which can allow for growth and differentiation of WAT or BAT cells. Adipose tissue can be readily assayed using routine techniques. An exemplary assay for adipose cells is the Oil Red O lipophilic red dye assay. The dye is used to stain neutral lipids in cells. The amount of staining is directly proportional to the amount of lipid in the cell and can be measured spectrophotometrically. The amount of lipid accumulation is determined as a parameter of differentiation. WAT and BAT can be distinguished by routine techniques, e.g., morphologic changes specific to WAT or BAT, or evaluation of WAT-specific or BAT-specific markers. For example, BAT cells can be identified by expression of uncoupling protein (UCP), e.g., UCP-1.

Necdin

Necdin is a 325-amino-acid residue protein encoded by a cDNA clone isolated from neurally differentiated embryonal carcinoma cells. Necdin is expressed in virtually all postmitotic neurons in the brain, and ectopic expression of necdin induces growth arrest of proliferative cells. Necdin binds to the transcription factors E2F1 and p53, which suggests that necdin may act through these cell-cycle-regulators.

See, e.g., OMIM entry No. *602117. The *homo sapiens* necdin polypeptide sequence is given at Genbank Acc. No. Q99608 (SEQ ID NO:1). The *homo sapiens* necdin gene, promoter and 5'UTR region are given at Genbank Acc. No. AF001013.1 (SEQ ID NO:2). The necdin gene lies within the Prader-Willi syndrome (PWS; OMIM 176270) deletion interval. PWS is characterized by diminished fetal activity, obesity, muscular hypotonia, mental retardation, short stature, hypogonadotropic hypogonadism, and small hands and feet.

A rabbit polyclonal antibody was raised against a bacterially expressed recombinant protein of a fragment of necdin. See Niinobe et al., *Dev. Neurosci.*, 22(4):310-319 (2000), who showed that necdin is enriched in the cytoplasm of hypothalamic neurons in fetal and adult mice, concentrated in the cytosolic fraction. This suggests that necdin is predominantly localized in the cytoplasm of differentiated cells, and moves into the nucleus under specific conditions, possibly to exert its effects on p53 and E2F1. Agents that inhibit this translocation therefore can be expected to inhibit necdin function.

Although Necdin expression was previously shown to be elevated in brown as compared to white adipocytes, the present results demonstrate that inhibition of necdin function allows differentiation of preadipocytes into brown adipocytes.

Inhibitors of Necdin Function

Described herein are methods for identifying and using inhibitors of Necdin function to promote BAT differentiation, thereby treating obesity. Thus, the invention includes necdin-inhibitory agents, including dominant negatives, antibodies and nucleic acid molecules that are targeted to Necdin RNA, e.g., antisense, siRNA, ribozymes, and aptamers.

siRNA Molecules

RNAi is a process whereby double-stranded RNA (dsRNA, also referred to herein as si RNAs or ds siRNAs, for double-stranded small interfering RNAs,) induces the sequence-specific degradation of homologous mRNA in animals and plant cells (Hutvagner et al., *Curr. Opin. Genet. Dev.*, 12"225-232 (2002); Sharp, *Genes Dev.*, 15:485-490 (2001)). In mammalian cells, RNAi can be triggered by 21-nucleotide (nt) duplexes of small interfering RNA (siRNA) (Chiu et al., *Mol. Cell*, 10:549-561 (2002); Elbashir et al., *Nature*, 411:494-498 (2001)), or by micro-RNAs (mRNA), functional small-hairpin RNA (shRNA), or other dsRNAs which are expressed in vivo using DNA templates with RNA polymerase III promoters (Zeng et al., *Mol. Cell*, 9:1327-1333 (2002); Paddison et al., *Genes Dev.*, 16:948-958 (2002); Lee et al., *Nature Biotechnol.*, 20:500-505 (2002); Paul et al., *Nature Biotechnol.*, 20:505-508 (2002); Tuschl, Nature Biotechnol., 20:440-448 (2002); Yu et al., Proc. Natl. Acad. Sci. USA, 99(9):6047-6052 (2002); McManus et al., RNA, 8:842-850 (2002); Sui et al., Proc. Natl. Acad. Sci. USA, 99(6):5515-5520 (2002)).

The nucleic acid molecules or constructs can include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can transcribed be in vitro from a DNA template, or in vivo from, e.g., shRNA. The dsRNA molecules can be designed using any method known in the art; a number of algorithms are known, and are commercially available. Gene walk methods can be used to optimize the inhibitory activity of the siRNA.

The nucleic acid compositions can include both siRNA and modified siRNA derivatives, e.g., siRNAs modified to alter a property such as the pharmacokinetics of the composition, for example, to increase half-life in the body, as well as engineered RNAi precursors.

siRNAs can be delivered into cells by methods known in the art, e.g., cationic liposome transfection and electroporation. siRNA duplexes can be expressed within cells from engineered RNAi precursors, e.g., recombinant DNA constructs using mammalian Pol III promoter systems (e.g., H1 or U6/snRNA promoter systems (Tuschl (2002), supra) capable of expressing functional double-stranded siRNAs; (Bagella et al., J. Cell. Physiol., 177:206-213 (1998); Lee et al. (2002), supra; Miyagishi et al., Nat. Biotechnol., 20(5): 497-500 (2002); Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into the cells with a vector expression T7 RNA polymerase (Jacque et al., Nature, 418:435-438 (2002)).

Antisense

An "antisense" nucleic acid can include a nucleotide sequence that is complementary to a "sense" nucleic acid encoding a protein, e.g., complementary to the coding strand of a double-stranded cDNA molecule or complementary to a target mRNA sequence. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence (e.g., the 5' and 3' untranslated regions).

An antisense nucleic acid can be designed such that it is complementary to the entire coding region of a target mRNA, but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of a target nucleic acid can be prepared, followed by testing for inhibition of target gene expression. Optionally, gaps of 5-10 nucleotides can be left between the oligonucleotides to reduce the number of oligonucleotides synthesized and tested.

In some embodiments, the antisense nucleic acid molecule is an α-anomeric nucleic acid molecule. An α-anomeric nucleic acid molecule forms specific double-stranded hybrids with complementary RNA in which, contrary to the usual β-units, the strands run parallel to each other (Gaultier et al., Nucleic Acids. Res., 15:6625-6641 (1987)). The antisense nucleic acid molecule can also comprise a 2'-o-methyhibonucleotide (Inoue et al., Nucleic Acids Res., 15:6131-6148 (1987)) or a chimeric RNA-DNA analogue (Inoue et al., FEBS Lett., 215:327-330 (1987)).

In some embodiments, the antisense nucleic acid is a morpholino oligonucleotide (see, e.g., Heasman, Dev. Biol., 243: 209-214 (2002); Iversen, Curr. Opin. Mol. Ther., 3:235-238 (2001); Summerton, Biochim. Biophys. Acta, 1489:141-158 (1999)).

Target gene expression can be inhibited by targeting nucleotide sequences complementary to a regulatory region (e.g., promoters and/or enhancers) to form triple helical structures that prevent transcription of the Spt5 gene in target cells. See generally, Helene, Anticancer Drug Des., 6:569-84 (1991); Helene, Ann. N.Y. Acad. Sci., 660:27-36 (1992); and Maher, Bioassays, 14:807-815 (1992). The potential sequences that can be targeted for triple helix formation can be increased by creating a so called "switchback" nucleic acid molecule. Switchback molecules are synthesized in an alternating 5'-3', 31-5' manner, such that they base pair with first one strand of a duplex and then the other, eliminating the necessity for a sizeable stretch of either purines or pyrimidines to be present on one strand of a duplex.

Ribozymes

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a target nucleic acid can include one or more sequences complementary to the nucleotide sequence of a cDNA described herein, and a sequence having known catalytic sequence responsible for mRNA cleavage (see Cech et al., U.S. Pat. No. 5,093,246 or Haseloff et al., *Nature,* 334:585-591 (1988)). For example, a derivative of a Tetrahymena L-19 IVS RNA can be constructed in which the nucleotide sequence of the active site is complementary to the nucleotide sequence to be cleaved in a target mRNA. See, e.g., Cech et al., U.S. Pat. No. 4,987,071; and Cech et al., U.S. Pat. No. 5,116,742. Alternatively, a target mRNA can be used to select a catalytic RNA having a specific ribonuclease activity from a pool of RNA molecules. See, e.g., Bartel et al., *Science,* 261:1411-1418 (1993).

Methods of Screening

Also included herein are methods for screening test compounds, e.g., lipids, polypeptides, polynucleotides, inorganic or organic large or small molecule test compounds, to identify agents that inhibit necdin function, which are useful in the treatment of disorders associated with increased necdin function, e.g., obesity.

Included herein are methods (also referred to herein as "screening assays") for identifying inhibitors, i.e., test compounds or agents (e.g., proteins, peptides, peptidomimetics, peptoids, small molecules or other drugs) that inhibit, e.g., statistically significantly inhibit, necdin function.

This can be accomplished, for example, by coupling one or both of necdin and a necdin-binding partner, e.g., p53 or E2f1, with a label, e.g., a radioisotope or non-isotopic, e.g., enzymatic, label, such that binding can be determined by detecting the labeled compound in a complex, e.g., in the presence and/or absence of a test compound, to monitor the ability of a test compound to modulate necdin binding to p53 and/or E2F1, or to affect subcellular localization of necdin. For example, necdin, p53 and/or E2F1 can be labeled with $^{125}$I, $^{35}$S, $^{14}$C, or $^{3}$H, either directly or indirectly, and the radioisotope can be detected by direct counting of radioemission or by scintillation counting. Alternatively, direct or indirect enzymatic labeling with, for example, biotin, horseradish peroxidase, alkaline phosphatase, or luciferase, can be used, and the enzymatic label detected by determination of conversion of an appropriate substrate to product. For example, biotin-necdin can be detected using an avidin-HRP stain.

The ability of necdin to interact with p53 and/or E2F1 with or without the labeling of any of the interactants can be evaluated. For example, a microphysiometer can be used to detect the interaction of necdin and p53 and/or E2F1 without the labeling of any of the interactants. See, e.g., McConnell et al., *Science,* 257:1906-1912 (1992). As used herein, a "microphysiometer" (e.g., Cytosensor®, Molecular Devices Corporation, Sunnyvale Calif.) is an analytical instrument that measures the rate at which a cell acidifies its environment using a light-addressable potentiometric sensor (LAPS). Changes in this acidification rate can be used as an indicator of the interaction between necdin and p53 and/or E2F1.

In some embodiments, the methods described herein include applying a test compound to a test sample including a cell or living tissue or organ, and evaluating one or more effects of the test compound, e.g., the ability of the test compound to disrupt necdin-activated signaling, e.g., signaling through p53 or E2F1, or subcellular localization of necdin, e.g., inhibition of translocation to the nucleus. Methods for detecting subcellular localization, e.g., fluorescence microscopy, and for evaluating signalling are known in the art.

In some embodiments, the test sample is, or is derived from (e.g., a sample originally taken from) an in vivo model of a disorder as described herein. For example, an animal model, e.g., a rodent such as a rat, that is obese can be used, and the ability of the test compound to improve one or more symptoms of the disorder, e.g., clinically relevant symptoms, e.g., weight, is evaluated.

A test compound that has been screened by a method described herein and determined to inhibit necdin function can be considered a candidate compound. A candidate compound that has been screened, e.g., in an in vivo model of a disorder, e.g., an obese animal, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Compounds that inhibit necdin function, e.g., that interfere with binding of necdin to p53 and/or E2F1, can be identified using, e.g., cell-based or cell free assays, as are known in the art. Such compounds can also be further screened in animal models.

Cell-Free Assays

Cell-free assays typically involve preparing a reaction mixture of necdin and the test compound under conditions and for a time sufficient to allow the two components to interact and bind, forming a complex that can be removed and/or detected. In some embodiments, necdin-binding proteins, e.g., p53 or E2F1, are also included in the mixture.

The interaction between two molecules can also be detected, e.g., using fluorescence energy transfer (FET) (see, for example, Lakowicz et al., U.S. Pat. No. 5,631,169; Stavrianopoulos et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor.' Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A FET binding event can be conveniently measured through standard fluorimetric detection means well known in the art (e.g., using a fluorimeter).

In another embodiment, determining the ability of necdin to bind to p53 and/or E2F1 can be accomplished using real-time Biomolecular Interaction Analysis (BIA) (see, e.g., Sjolander et al., *Anal. Chem.,* 63:2338-2345 (1991); Szabo et al., *Curr. Opin. Struct. Biol.,* 5:699-705 (1995)). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In some embodiments, either necdin, p53 and/or E2F1 is anchored onto a solid phase. The necdin and p53 or E2F1 complexes anchored on the solid phase can be detected at the end of the reaction. For example, necdin can be anchored onto a solid surface, and p53, (which is not anchored), can be labeled, either directly or indirectly, with detectable labels discussed herein.

In some embodiments, the assay is an Enzyme Linked Immuno-Sorbent Assay (ELISA). Such assays have the advantage of being generally cheap, fast and automatable. For example, p53 or E2F1 can be immobilized on plastic, and binding of biotin-necdin can be detected using an avidin-HRP stain, or vice-versa. Test compounds can be assayed to see if they affect binding, e.g., if binding of biotin-necdin or fluorescent-p53 can no longer be detected or is significantly reduced.

Thus, it may be desirable to immobilize necdin and p53 and/or E2F1 to facilitate separation of complexed from uncomplexed forms of one or both of the proteins, as well as to accommodate automation of the assay. Binding of necdin to p53 or E2F1, e.g., in the presence and absence of a candidate compound, can be accomplished in any vessel suitable for containing the reactants. Examples of such vessels include microtiter plates, test tubes, and micro-centrifuge tubes.

In some embodiments, a fusion protein can be used that adds a domain that allows the necdin and p53 and/or E2F1 protein to be, e.g., bound to a matrix. For example, glutathione-S-transferase fusion proteins can be adsorbed onto glutathione Sepharose™ beads (Sigma Chemical, St. Louis, Mo.) or glutathione derivatized microtiter plates. The coated surfaces can then be combined with a test compound, or a test compound and either the non-adsorbed reactant(s), and the mixture incubated under conditions conducive to complex formation (e.g., at physiological conditions for salt and pH as described herein). Following incubation, the beads or microtiter plate wells are washed to remove any unbound components, the matrix immobilized in the case of beads, and the presence of complexes determined either directly or indirectly, for example, as described above. Alternatively, the complexes can be dissociated from the matrix, and the level of necdin and p53 or E2F1 binding can be determined using known techniques.

Other techniques for immobilizing necdin, p53 and/or E2F1 on matrices include using conjugation of biotin and streptavidin. Biotinylated necdin, p53 and/or E2F1 can be prepared from biotin-NHS(N-hydroxy-succinimide) using techniques known in the art (e.g., using biotinylation kits available from Pierce Chemicals, Rockford, Ill.), and immobilized in the wells of streptavidin-coated 96 well plates (Pierce Chemical).

High protein binding plastic substrates can also be used; the species to be immobilized is simply adsorbed to the plastic. These substrates do not require any modification of the species to be immobilized. Suitable substrates are commercially available and include multi-well plates, e.g., Microlon® ELISA 96-well Immunoassay Plates (Bellco Glass, Inc., Vineland, N.J.), EIA/RIA Immunoassay Plates (E&K Scientific, Campbell, Calif.).

To conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways known in the art. For example, where the previously non-immobilized component is pre-labeled, the detection of label immobilized on the surface indicates that complexes were formed.

Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody). In embodiments where one reactant is biotinylated, detection can be with avidin-HRP.

In some embodiments, this assay is performed utilizing necdin-, p53- and/or E2F1-specific binding proteins, e.g., antibodies, that do not interfere with binding of necdin to p53 and/or E2F1, depending on which is being assayed. Such specific binding proteins can be derivatized to a surface, e.g., beads or the wells of a plate, and unbound necdin, p53 and/or E2F1 trapped in the wells by antibody conjugation. Methods for detecting such complexes, in addition to those described above for the GST- or protein-A immobilized complexes, include immunodetection of complexes using antibodies reactive with the necdin, p53 and/or E2F1, as well as enzyme-linked assays that rely on detecting an enzymatic activity associated with the necdin, p53 and/or E2F1.

Alternatively, cell free assays can be conducted in a liquid phase. Generally, in such an assay, the reaction products are separated from unreacted components, by any of a number of standard techniques, including but not limited to: differential centrifugation (see, for example, Rivas et al., *Trends Biochem. Sci.*, 18:284-287 (1993)); chromatography (gel filtration chromatography, ion-exchange chromatography); electrophoresis (see, e.g., Ausubel et al., eds., *Current Protocols in Molecular Biology*, J. Wiley, New York (1999)); and immunoprecipitation (see, for example, Id.). Suitable resins and chromatographic techniques are known to one skilled in the art (see, e.g., Heegaard, *J. Mol. Recognit.*, 11:141-148 (1998); Hage et al., *J. Chromatogr. B Biomed. Sci. Appl.*, 699:499-525 (1997)). Further, fluorescence energy transfer can also be conveniently utilized, as described herein, to detect binding without further purification of the complex from solution.

Alternatively or in addition, a test compound can be screened to determine if it affects the Kd of an interaction between necdin and p53 and/or E2F1. For example, a test sample including necdin and p53 and/or E2F1 can be incubated in the presence of a test compound; a control sample can include no test compound, and/or a compound that is known to interfere with binding of necdin to p53 and/or E2F1. The surface can be used to collect the necdin and p53 or E2F1 complexes (e.g., by centrifugation in the case of beads), and binding can be detected. For example, a 6×His tagged necdin can be used, and binding can be detected using Ni-HRP, by measuring the absorbance of each sample at 450 nm.

To identify compounds that interfere with an interaction between necdin and p53 and/or E2F1, a reaction mixture containing necdin and p53 and/or E2F1 is prepared, and incubated under conditions and for a time sufficient, to allow the two products to form complex. To test an inhibitory agent, the reaction mixture is analyzed in the presence and absence of the test compound. The test compound can be initially included in the reaction mixture, or can be added at a time subsequent to the addition of the target gene and its cellular or extracellular binding partner. Control reaction mixtures are typically incubated without the test compound or with a negative control, or with a positive control compound known to interfere with the interaction between necdin and p53 and/or E2F1. The formation of any complexes between necdin and p53 and/or E2F1 is then detected. The formation of a complex in the control reaction, but not in the reaction mixture containing the test compound, indicates that the compound interferes with the interaction of the target gene product and the interactive binding partner.

In an alternate embodiment of the invention, a homogeneous assay can be used in which a preformed complex of the necdin and p53 and/or E2F1 is prepared, in which either necdin, p53 and/or E2F1 is labeled, but the signal generated by the label is quenched due to complex formation (see, e.g., Allemann et al., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

Cell-Based Assays

The assays described herein can also be performed in samples including cells. Cell-based assays are known in the art, and can be used, e.g., to detect binding of necdin to p53 and/or E2F1, and/or effects that occur downstream, e.g., in a cell expressing necdin, p53 and/or E2F1, whether a test compound affects a downstream effect of necdin signalling. Downstream effects of necdin signalling include cell proliferation, p53 and E2F1 signalling, formation of BAT, and translocation of necdin to the nucleus. For example, a cell that expresses necdin can be used, and fluorescence microscopy analysis can be used to detect changes in subcellular localization of labeled necdin; for example, necdin directly conjugated with a fluorochrome a tag, such as FLAG, that can be detected using an antitag (e.g., anti-FLAG) antibody or similar chemistry. Molecules that interfere with binding should give lower fluorescence intensities in the histograms.

In some embodiments, the methods can include screening a test compound in a first, e.g., cell-free, assay, to identify compounds that can inhibit binding of necdin to p53 and/or E2F1, and then in a second, e.g., cell-based, assay, to identify those compounds that inhibit the downstream effects of necdin signalling, e.g., activation of p53 and/or E2F1. In some embodiments, cellular activation is monitored using FACS to follow upregulation of BAT markers.

Animal Models

Also included herein are methods of screening compounds by administering a compound, e.g., a compound identified in a cell-free or cell-based screen as described herein as a compound that can inhibit necdin function to an animal model of obesity. Suitable animal models are known in the art. The methods include administering at least one dose of a compound to the animal, and monitoring the animal for an effect of the compound on the disorder in the animal, e.g., an effect on a clinically relevant parameter, e.g., a parameter that is related to a clinical symptom of the disease as described herein, e.g., weight, or amount of BAT versus WAT. Methods for selecting, evaluating and scoring such parameters are known in the art.

Methods of Prevention and Treatment

The methods described herein include methods for the prevention and treatment of disorders associated with necdin signalling, e.g., obesity. Generally, the methods include administering a therapeutically effective amount of a therapeutic composition, e.g., a composition including an inhibitor of necdin function as an active ingredient, as described herein, to a subject who is in need of, or who has been determined to be in need of, such treatment.

As used in this context, to "treat" means to ameliorate at least one symptom of the disorder, e.g., to reduce weight and/or body mass index.

In some embodiments, the methods include preventive methods, e.g., methods including administering a therapeutically effective amount of a composition described herein to a subject who is at risk of becoming obese, e.g., subjects at the highest risk for developing obesity, such as those with a family history of sever obesity.

Dosage, toxicity, and therapeutic efficacy of the compounds can be determined, e.g., by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods described herein, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

An "effective amount" is an amount sufficient to effect beneficial or desired results. For example, a therapeutic amount is one that achieves the desired therapeutic effect, e.g., weight loss. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

Pharmaceutical Compositions and Methods of Administration

The therapeutic compounds described herein can be incorporated into pharmaceutical compositions. Such compositions typically include the nucleic acid molecule and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

For administration by inhalation, the compounds are typically delivered in the form of an aerosol spray from pressured container or dispenser which contains a suitable propellant, e.g., a gas such as carbon dioxide, or a nebulizer. Such methods include those described in Debs et al., U.S. Pat. No. 6,468,798.

The therapeutic compounds can also be prepared in the form of suppositories (e.g., with conventional suppository bases such as cocoa butter and other glycerides) or retention enemas for rectal delivery.

Therapeutic compounds comprising nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in Johnston et al., U.S. Pat. No. 6,194,389, and the mammalian transdermal needle-free vaccination with powder-form vaccine as disclosed in Bellhouse et al., U.S. Pat. No. 6,168,587. Additionally, intranasal delivery is possible, as described in, inter alia, Hamajima et al., *Clin. Immunol. Immunopathol.*, 88(2):205-210 (1998). Liposomes (e.g., as described in Hoon et al., U.S. Pat. No. 6,472,375) and microencapsulation can also be used. Biodegradable targetable microparticle delivery systems can also be used (e.g., as described in Sokoll et al., U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in Eppstein et al., U.S. Pat. No. 4,522,811.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

The pharmaceutical compositions can be included in a container, pack, or dispenser together with instructions for administration.

EXAMPLES

The invention is further described in the following examples, which do not limit the scope of the invention described in the claims.

Materials

The pGL3 γ1 reporter gene construct and expression vectors for E2F1, E2F4 and DP-1 were generous gifts of Dr. Llus Fajas (Metabolism and Cancer Laboratory, INSERM, France) (Fajas et al., *Dev. Cell,* 3:39-49 (2002)). Expression constructs of full-length necdin cDNA, the truncated necdin mutant and anti-necdin antibody were provided by Drs. Michio Niinobe and Kazuaki Yoshikawa (University of Osaka, Japan) (Taniura et al., *J. Biol. Chem.,* 273:720-728 (1998); Kobayashi et al., *J. Biol. Chem.,* 277:42128-42135 (2002)). Plasmid encoding constitutively active mutant of CREB was a gift of Dr. Marc Montminy (Salk Institute, La Jolla, Calif.) (Asahara et al., *Mol. Cell. Biol.,* 21:7892-7900 (2001)). The E2F1 and E2F4 and Pref-1 antibodies were purchased from Santa Cruz Biotechnology (Santa Cruz, Calif.). Anti-phospho-CREB (Ser133) and anti-CREB antibodies were purchased from Cell Signaling Technology (Beverly, Mass.). Monoclonal antibodies against ubiquinol-cytochrome c oxidoreductase (core I subunit) and ATP synthase (β subunit) were purchased from Molecular Probes (Eugene, Oreg.). Human recombinant IGF-1 was obtained from Pepro Tec. Inc. (Rocky Hill, N.J.). Chemicals were obtained from Sigma (St. Louis, Mo.) unless otherwise specified.

Cell Culture and Differentiation

Generation of brown preadipocyte cell lines derived from newborn WT and IRS KO mice was as described previously (Tseng et al., *J. Biol. Chem.,* 277:31601-31611 (2002)). Preadipocytes were grown to confluence (day 0) in differentiation medium (Dulbeco's modified Earle's medium containing 10% fetal bovine serum supplemented with 20 nM insulin and 1 nM T3). Adipocyte differentiation was induced by treating confluent cells for 48 hours in differentiation medium further supplemented with 0.5 mM isobutylmethylxanthine (IBMX), 0.5 µM dexamethasone, and 0.125 mM indomethacin. After this induction period (day 2), cells were changed back to differentiation medium, which was then changed every second day. After four more days in differentiation medium (day 6), cells exhibited a fully differentiated phenotype with massive accumulation of multi-locular fat droplets as identified by Oil Red O staining (Tseng et al., *Mol. Cell. Biol.,* 24:1918-1929 (2004)).

To evaluate CREB phosphorylation in response to acute IGF-1 stimulation, cells were grown on a 100-mm dish to about 90% confluent and were serum deprived overnight in medium containing 0.1% BSA and then treated for 5 minute with IGF-1 at a final concentration of 10 nM.

Reconstitution of IRS-1 in IRS-1 KO Cells

The IRS-1 reconstitution in IRS-1 KO cells was generated using retroviral-mediated gene transfer (Fasshauer et al., *Mol. Cell. Biol.,* 21:319-329 (2001)). Briefly, 3 µg of pBABE retroviral vector encoding human IRS-1 was transfected into ΦNX-packaging cells in 6-cm-diameter plates using the calcium phosphate method (Morgenstern et al., *Nucleic Acid Res.,* 18:3587-3596 (1990)). The cells were refed 10 hours later, and viral supernatants were harvested 48 hours after transfection. KO cells were infected at 70% confluence in a 12-well plate with polybrene (8 µg/ml)-supplemented virus-containing supernatant for overnight. 48 hours after infection, cells from each well were trypsinzed and transferred to a 15-cm-diameter plate. Stable cell lines were established by selection in medium containing 250 µg/ml of the bleomycin analogue, Zeocine (Invitrogen).

Microarray Analysis

Brown preadipocytes were grown to confluence and synchronized by overnight serum starvation. Total RNA was isolated with ULTRASPEC RNA Isolation System (Biotecx Laboratories, Inc., Houston, Tex.) following the manufacture's instruction. Four independent RNA samples were analysed from each IRS KO cell line, and in all cases RNA from two independent KO cell lines were pooled for each chip analysis. In addition, three independent clones of WT cells (littermates for IRS-1 KO, IRS-2 KO, and IRS-3 KO) were separately analysed as controls. This resulted in a total 28 microarrays used in this study. 28 µg of total RNA were subjected to cDNA and cRNA preparations as previously described (Yechoor et al., *Proc. Natl. Acad. Sci. USA,* 99:10587-10592 (2002)). 15 µg of adjusted cRNA were hybridised to Affymetrix U74A-v2 arrays (Santa Clara, Calif.). Intensity values were quantitated by MAS 5.0 software (Affymetrix). All chips were subjected to global scaling to a target intensity of 1, 500 to take into account the inherent differences between the chips and their hybridization efficiencies.

Two criteria were used for data analysis to select genes with potential of strong impact on adipogenesis. In the first criteria, we compared genes whose expression was significantly altered at the basal state between WT (4 arrays) and IRS-1 KO (4 arrays) brown preadipocytes, the two genotypes that exhibited the most severe difference in phenotype. For each gene, we examined the hypothesis $H_1$: $m_{g,wt} \neq m_{g,irs1ko}$ against $H_0$: $m_{g,wt} = m_{g,irs1ko}$ where $m_{g,x}$ indicates the mean expression level for gene g in samples obtained from mice with genotype x, and wt indicates WT littermates for the IRS-1 KO mice (4 samples). Significance was determined for each gene through the calculation of a p-value ($p_{irs}$) using the Student's t-test with unpaired values and the Welch correction for unequal variance, implemented as described in Press et al., eds., *Numerical Recipes in C: The Art of Scientific Computing,* Cambridge University Press, Cambridge (1993). As recommended by Pan et al., *Genome Biol.,* 3:research0022 (2002), we did not assume equal variance between the two groups, since previous publications have demonstrated that variance in gene expression measurements might be a function of expression level (Ideker et al., *J. Comput. Biol.,* 7:805-817 (2000)).

The threshold of $p_{irs} < 0.01$ was chosen based on the data in consideration of multiple comparisons in the following manner. The sample labels (WT and IRS-1 KO) for the data set of gene expression values were randomly permuted 100 times, and the genes were subjected to the same t-tests each time. A q-value ($q_{irs}$) was then calculated for each gene, based on the ratio of number of false positives we would expect over the total number of significant genes if the gene were called significant (Storey and Tibshirani, Proc. Natl. Acad. Sci. USA, 100:9440-9445 (2003)). We plotted $q_{irs}$ versus the number of significant genes if each q-value were used as the threshold and noted several regions of the curve where the number of significant genes increased with little change in $q_{irs}$. Using a previously described heuristic, we noted one of these regions at $q_{irs} < 0.44$, corresponding to $p_{irs} < 0.01$, and used this to set our $p_{irs}$ threshold (FIG. 8) (Storey and Tibshirani, *Proc. Natl. Acad. Sci. USA,* 100:9440-9445 (2003)). The $p_{irs}$ and $q_{irs}$ values for some of the significant genes are reported in Table 1.

Figure 1:
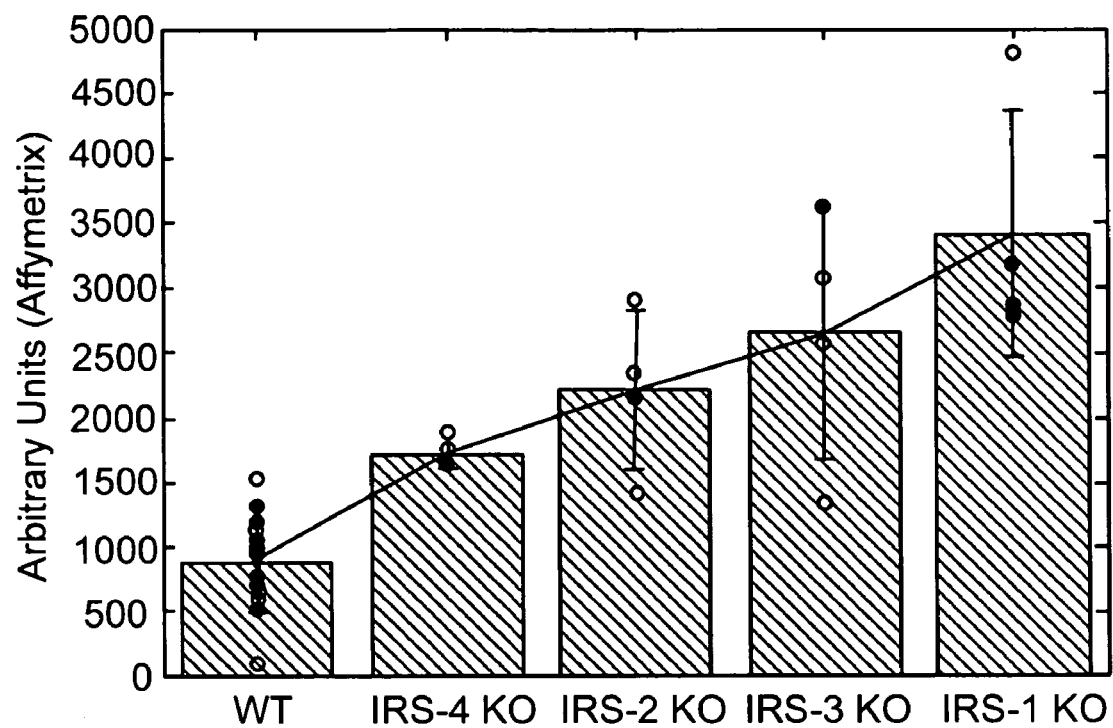
FIG. 1 is a bar graph illustrating expression of Trib3, which was progressively increased in cells with increasing defects in differentiation.

To further define the relationship between the altered gene expression and the potential to differentiate, we added a second, more conservative criterion. This involved selection of those genes whose expression patterns in all four IRS KO brown preadipocytes and all WT littermates correlated with the continuum of phenotypes of the potential for adipocyte differentiation (FIG. 1). Specifically, for each gene g we examined the hypothesis $H_1: m_{g,pooled-wt} \leq m_{g,irs4ko} \leq m_{g,irs2ko} \leq m_{g,irs3ko}$
$\leq m_{g,irs1ko}$ (up-progression)

against $H_0: m_{g,pooled-wt} = m_{g,irs4ko} = m_{g,irs2ko} = m_{g,irs3ko} = m_{g,irs1ko}$ where $m_{g,x}$ indicates the mean expression level for gene g in samples obtained from mice with genotype x, pooled-wt indicates all WT littermates (12 samples), and where one of the inequality signs must be a strict inequality. We calculated the test statistic $\bar{F}_k$ using a program implemented exactly as described by Bartholemew and validated using Bartholemew's sample data (Bartholemew, *Biometrika*, 46:36-48 (1959)). Similarly, we calculated a separate test statistic for the hypothesis $H_1: m_{g,pooled-wt} \geq m_{g,irs4ko} \geq m_{g,irs2ko} \geq m_{g,irs3ko}$
$\geq m_{g,irs1ko}$ (down-progression)

against $H_0: m_{g,pooled-wt} = m_{g,irs4ko} = m_{g,irs2ko} = m_{g,irs3ko} = m_{g,irs1ko}$ Two separate calculations were performed scoring both an up- and down-progression for each gene. P-values were determined using the resultant $\bar{F}_k$ scores and the F-distribution. To test the underlying assumptions in our data using Bartholemew's test of homogeneity for ordered alternatives, we tested for homogeneity of variances using Levene's test and determined that for 15% of the genes, the p-value from Levene's test was under 0.05, indicating that the null hypothesis of homogenous variances would be rejected (Levene, In *Contributions to Probability and Statistics: Essays in Honor of Harold Hotelling*, Stanford University Press, pp. 278-292 (1960)). In addition, we also note that the pooled-WT group contains significantly more samples than any of the other genotype groups. Both of these limitations commonly restrict the interpretation of an ANOVA test, and must be considered when interpreting the results of the Bartholemew's test.

To control for multiple comparisons, q-values ($q_{up}$ and $q_{down}$) were calculated in a process similar to the one described above. The five sample labels (WT and IRS-1, -2, -3, -4 KO) were randomly permuted 100 times, the genes were subjected to the same Bartholemew's test each time, and $q_{up}$ and $q_{down}$ were computed as the ratio of number of false positives we would expect over the total number of significant genes if the gene were called significant. We plotted $q_{up}$ and $q_{down}$ versus the number of significant genes if each q-value were used as the threshold and chose the region $q_{up}$ and $q_{down}<0.03$, which corresponds to $p_{up}<0.27$ and $p_{down}<0.47$ (FIG. 8). The $q_{up}$ and $q_{down}$ values for some of the significant genes are reported in Table 1.

We acknowledge that the threshold $q_{irs}$ close to 0.5 is higher than used in some microarray analyses, and reflects the number of microarrays measured in each category. This was part of our decision to use the power of the genetics and phenotypes by measuring more genotypes with fewer microarrays, rather than more microarrays in fewer genotypes. As would be expected, there are more significant genes at the lower thresholds $q_{up}$ and $q_{down}$ for the progression analysis because of the increased number of samples available for that analysis. In addition, we performed extensive biological functional validation for these genes, leading to the findings in this study. Since experimental validation was necessary, as well as studies of the function of some of the genes in adipogenesis, we were willing to accept a somewhat higher false-positive rate on the basis that distinguishing true positives from false positives was a task we were willing to undertake a priori.

In addition, power is an issue that must be considered. The a priori use of power to calculate the number of replicates needed has been described in an increasing number of publications, but even the authors of these publications note that it is difficult to answer questions about sample size and power when the criteria for selection of genes (e.g. a p-value threshold based on a false-discovery rate) and the variance of gene expression measurements are not known in advance (Pan et al., *Genome Biol.*, 3:research0022 (2002); Yang et al., *Nat. Rev. Genet.*, 3:579-588 (2002)). We had no a priori estimates on the number of genes whose expression may be different between genotypes, and we have no concrete information about the power of the study to detect effects of interest or those plausibly hypothesized to exist, so our study may have been grossly underpowered, markedly overpowered, or adequately powered.

All permutation was done by assigning each sample label to be permuted a random number from a uniform distribution, and sorting by this number to shuffle those labels.

18 genes were selected for Q-RT-PCR validation (see below) based on $p_{irs}$ value or biological interests. Of these, 11 genes show concordant (i.e. same direction) and significant changes (61.1%). In the remaining 7 selected genes, expression of 4 genes was still concordant with array data. Thus, a total of 15 out of 18 genes assessed (83.3%) showed concordant changes in Q-RT-PCR and the microarray analysis.

Quantitative Reverse Transcription-Polymerase Chain Reaction (Q-RT-PCR) Analysis cDNA was prepared from 1 µg of RNA using the Advantage RT-PCR kit (BD Biosciences, Palo Alto, Calif.) according to manufacturer's instructions. 5 µl of cDNA was used in a 40 µl PCR reaction (SYBR Green, PE Biosystems, Foster City, Calif.) containing primers at a concentration of 300 nM each. PCR reactions were run in triplicate and quantitated in the ABI Prism 7700 Sequence Detection System. Results were expressed as arbitrary mRNA units. Sequences of primers used in this study can be found in

TABLE 2

Table 2: Primer sequences of genes validated by quantitative RT-PCR

| Gene | Applications | Sequences | Gene | SEQ ID NO: |
|---|---|---|---|---|
| Necdin | Taqman | Forward | GAGTTTGCCCTGGTCAAAGC | 3 |
|  |  | Reverse | CATGGGCATACGGTTGTTGAG | 4 |
|  |  | Probe | CACCCTGTCTAGCTCCTCTGGGCTGA | 5 |
| GATA-3 | Sybr-Green | Forward | CTTATCAAGCCCAAGCGAAG | 6 |
|  |  | Reverse | CAGGGATGACATGTGTCTGG | 7 |

TABLE 2-continued

Table 2: Primer sequences of genes validated by quantitative RT-PCR

| Gene | Applications | Sequences | Gene | SEQ ID NO: |
|---|---|---|---|---|
| PPARg | Sybr-Green | Forward | TCAGCTCTGTGGACCTCTCC | 8 |
|  |  | Reverse | ACCCTTGCATCCTTCACAAG | 9 |
| sFRP-2 | Sybr-Green | Forward | AGGACAACGACCTCTGCATC | 10 |
|  |  | Reverse | GTACGTTATCTCCTTCACTTTG | 11 |
| Pref-1 | Sybr-Green | Forward | AGTACGAATGCTCCTGCACAC | 12 |
|  |  | Reverse | CTGGCCCTCATCATCCAC | 13 |
| PGC-1a | Sybr-Green | Forward | GTCAACAGCAAAAGCCACAA | 14 |
|  |  | Reverse | TCTGGGGTCAGAGGAAGAGA | 15 |
| Gjb3 | Sybr-Green | Forward | AGACCTATTGAGTGGCGTGAA | 16 |
|  |  | Reverse | TGTTGGAGATGGGGAAGAAG | 17 |
| TRB3 | Sybr-Green | Forward | CTTTTGGAACGAGAGCAAGG | 18 |
|  |  | Reverse | AAAGATATAAAGGAGCCGAGAG | 19 |
| Mef2c | Sybr-Green | Forward | AGGACAAGGAATGGGAGGA | 20 |
|  |  | Reverse | GTGTTGTGGGTATCTCGAAGG | 21 |
| Wnt10a | Sybr-Green | Forward | CACCCGGCCATACTTCCT | 22 |
|  |  | Reverse | CACTTACGCCGCATGTTCT | 23 |
| Wnt6 | Sybr-Green | Forward | GCTGCTGCTGCTCTTGTG | 24 |
|  |  | Reverse | TCGGAAACGGAACTGGAA | 25 |
| Wnt5a | Sybr-Green | Forward | GGTTGTTATAGAAGCTAATTCTTGG | 26 |
|  |  | Reverse | GCATTCCTTGATGCCTGTCT | 27 |
| TCF7 | Sybr-Green | Forward | CTCCTCTCTACCCCCTGTCC | 28 |
|  |  | Reverse | TTGGGTTCTGCCTGTGTTTT | 29 |
| Wisp-1 | Sybr-Green | Forward | CGTGGAGCAACGGTATGAG | 30 |
|  |  | Reverse | TCCCTGCCTTGATGTGTAGTT | 31 |
| Col6a1 | Sybr-Green | Forward | ATTAAGAAGGGGCTGGAGGA | 32 |
|  |  | Reverse | AGGTGGTCAGGTGTGATGG | 33 |
| FABP4 | Sybr-Green | Forward | AATGTGTGATGCCTTTGTGG | 34 |
|  |  | Reverse | ACGCCCAGTTTGAAGGAA | 35 |

Transfection and Reporter Gene Assay

Brown preadipocytes were plated at $1 \times 10^5$/well of 12-well plates 18 hours before transfection. Cells were transfected by LF2000 reagent ((Invitrogen, Carlsbad, Calif.) with 2 µg of pGL3 γ1 reporter construct, 1 µg of expression vectors for DP-1, E2F1, E2F4, necdin and the truncated necdin mutant, and 0.5 µg of a promoterless *Renilla* luciferase construct (pRL-0). Cells were lysed 48 hours after transfection with 200 µl per well of 1× passive lysis buffer (Promega, Madison, Wis.). Luciferase activity was measured by using 20 µl of lysates and the Dual-Luciferase Reporter Assay System (Promega) following manufacture's instruction. Relative light units were determined by quantitation of the signal from the Firefly luciferase normalized with co-transfected *Renilla* luciferase activity in the same sample. Finally, these relative values were normalized vs. mock transfection. Each expression construct was transfected in triplicate wells. The experiments were repeated three times.

Inhibitory Short Hairpin RNA (RNAi) of Necdin

The necdin mRNA sequence was analysed for selecting inhibitory RNA sequences using generally accepted design rules, and a 19-nucleotide (nt) sequence run commencing from nt 1203-1222 was selected. This sequence was synthesized as a double-stranded oligonucleotide containing the indicated sequence shown below, an 8 nt loop sequence, the reverse complement of the sequence, followed by a pentathymidine termination sequence. To allow for cloning into the U6 vector, an XhoI compatible end was added to the 5' end and an XbaI site was added to the 3' end. The oligonucleotide sequences are as follows:

```
forward  TCGAGgagtatcccaaatggacagttcaagagactgtccatttgggatactcTTTTT   36
reverse  CTAGAAAAAgagtatcccaaatggacagtctcttgaactgtccatttgggatactcC    37
```

The forward and reverse oligos were annealed and ligated into a vector containing the human U6 promoter (Imgenex, IMG-800, San Diego, Calif.). This construct as well as a vector encoding an unrelated RNAi were co-transfected along with a vector encoding a bleomycin resistant gene into IRS-1 KO brown preadipocytes at a ratio 3:1 by LF2000 reagent (Invitrogen) and selected with 250 μg/ml of the bleomycin analogue Zeocin (Invitrogen) 48 hours after transfection.

Western Blot Analysis

Cells grown on a 100-mm dish were washed twice with ice-cold phosphate-buffered saline and scraped into 0.5 ml of lysis buffer as previously described (Tseng et al., *Mol. Cell. Biol.*, 24:1918-1929 (2004)). Protein concentrations were determined using the Bradford protein assay (Bio-rad). Lysates (30-50 μg) were subjected to SDS-PAGE followed by immunoblotting using specific antisera and detection with chemiluminescence (ECL, Amersham Pharmacia Biotech, Piscataway, N.J.).

Example 1

Search Strategy

The present inventors previously reported that brown preadipocytes derived from wild-type (WT) and different IRS KO animals exhibited a progressive defect in adipocyte differentiation (Tseng et al., *Mol. Cell. Biol.*, 24:1918-1929 (2004)), such that WT and IRS-4 KO cells fully differentiate into mature adipocytes; IRS-2 KO cells exhibit a slight decrease in differentiation; IRS-3 KO cells show a moderate defect; and IRS-1 KO cells exhibit a severe defect in differentiation. This occurs not only at the levels of lipid accumulation, but also involves blockade of the normal pattern of progression in the transcriptional regulators of adipogenesis, such as C/EBPα and PPARγ. We hypothesized that these defects in differentiation potential were programmed in preadipocytes by alterations of gene expression, linking to the defects in insulin/IGF-1-mediated signalling. To test this hypothesis, we measured basal gene expression in preadipocytes of each KO and WT cell line using Affymetrix microarrays.

To define genes that have potential impact on determination of preadipocyte differentiation, microarray data were analysed using two approaches (FIG. 1 and *Methods* for details). In the first approach, we compared genes whose expression was significantly altered in the basal state between IRS-1 KO brown preadipocytes and preadipocytes from WT littermates, the two genotypes that exhibited the most severe difference in phenotype. A total of 284 probe-sets corresponding to 276 genes/ESTs passed this statistical filter with p value ($p_{irs}$)<0.01 using a Student's t-test for unpaired values with Welch correction for unequal variance (FIG. 10).

Figure 8A:
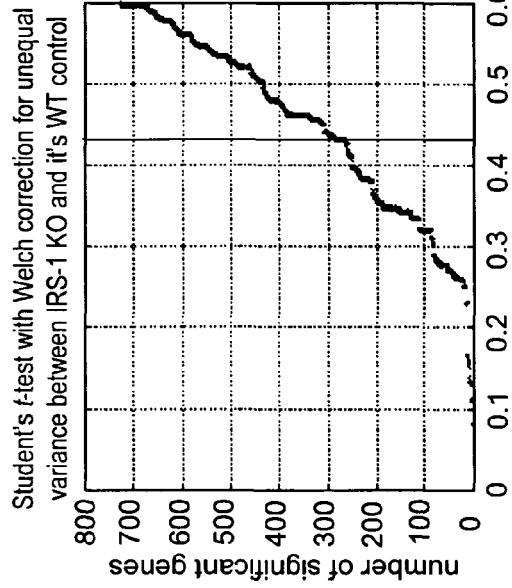
FIGS. 8A-D are line graphs illustrating the results of Student's t-test with Welch correction for unequal variance between WT and IRS-1 KO cells.
Figure 8B:
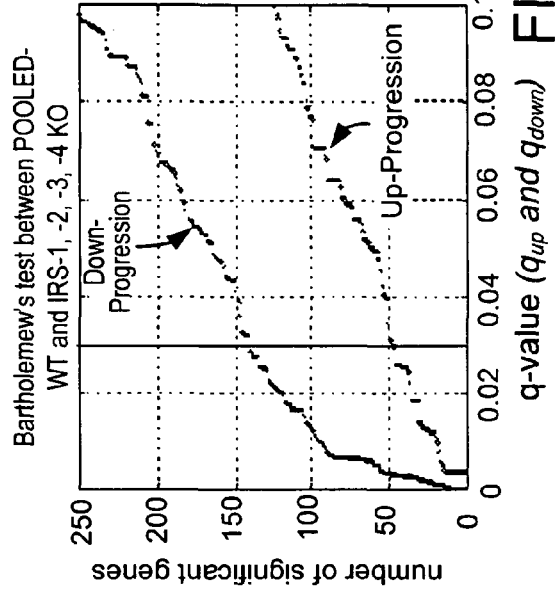
Figure 8C:
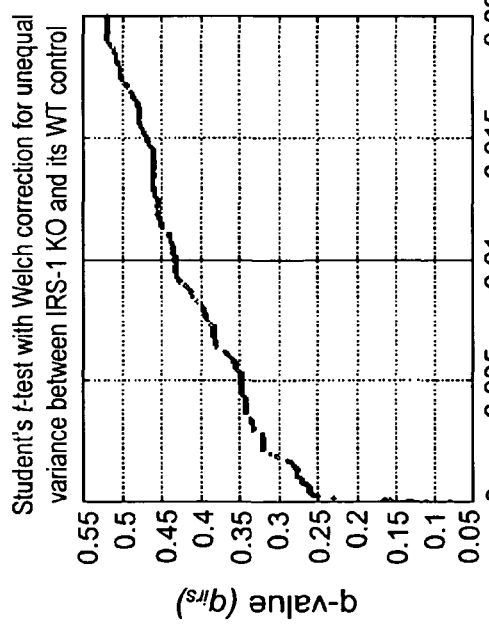
Figure 8D:
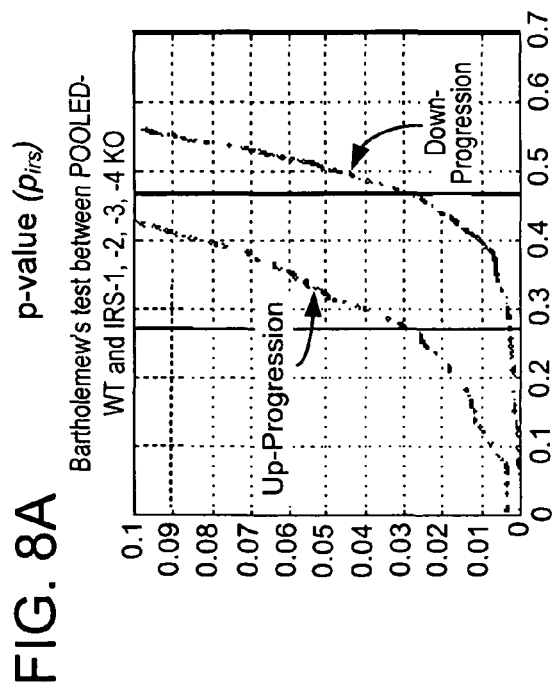

To assess the effect of multiple comparisons, a q-value ($q_{irs}$) was calculated for each gene, based on the proportion of false positives we would expect if the gene were called significant. FIG. 8B shows that at $q_{irs} \approx 0.44$, one finds a region of the curve where one can add a number of significant genes at little expense to q-value. The point of $q_{irs}$<0.44 corresponds to $p_{irs}$<0.01, as shown in FIG. 8A. Each gene was assigned a $p_{up}$ and $p_{down}$ based on the likelihood of an ordering of increasing or decreasing mean expression levels corresponding to increasing degree of difficulty of adipogenesis across the genotypes, using Bartholemew's test of homogeneity for ordered alternatives, and $q_{up}$ and $q_{down}$ were in a manner similar to $q_{irs}$. The point of $q_{up}$ and $q_{down}$<0.03 (D), corresponding to $p_{up}$<0.27 and $p_{down}$<0.47 FIG. 8C, was used as the threshold.

This corresponded to a q value ($q_{irs}$)<0.44 (FIG. 8), where the q value was calculated for each gene based on the ratio of number of false positives we would expect over the total number of significant genes if the genes were called significant (Storey and Tibshirani, *Proc. Natl. Acad. Sci. USA*, 100: 9440-9445 (2003)). To help further define the most relevant changes in gene expression with regard to potential for preadipocyte conversion to adipocytes, we added a second, more stringent criterion by searching for genes whose basal expression patterns in all four KO preadipocytes and all WT littermates correlated with the phenotypic continuum of ability to undergo adipocyte differentiation (FIG. 1, bottom). Genes were chosen as meeting this criteria if the ordering of expression levels across the five types of preadipocytes was either WT≧IRS-4 KO≧IRS-2 KO≧IRS-3 KO IRS-1 KO or the reverse WT≦RS-4 KO≦IRS-2 KO≦IRS-3 KO≦IRS-1 KO, as defined by Bartholemew's test of homogeneity for ordered alternatives (Bartholomew, *Biometrika*, 46:36-48 (1959)). The significance of these ordered changes is referred to hereafter as $p_{up}$, $p_{down}$, $q_{up}$, and $q_{down}$. A total of 190 probe-sets corresponding to 181 genes/ESTs passed the criteria in this second approach, and 82 genes/ESTs passed both the first and second criteria (FIGS. 1 and 2).

Of these 82 genes, 32 genes exhibited a pattern of increasing expression with decreasing ability in differentiation, while 50 genes showed the opposite pattern. These genes were then assigned into different functional categories (see below). Interestingly, many of these genes are known to be involved in different early adipogenic events, suggesting the power of this genomic approach to define gene expression signatures of preadipocytes can be used as a surrogate to predict the outcome of differentiation.

Example 2

Multiple Genes Involved in Morphological Modification are Altered in Preadipocytes with Impaired Ability in Differentiation Both the normal progression of cells from preadipocytes to adipocytes and the blockade in this process in the IRS KO cells appear to involve coordinated patterns of gene expression. Thus, the first hallmark during the early stage of adipogenesis is the dramatic change in morphology as the cells convert from fibroblastic to spherical shapes (Gregoire, *Exp. Biol. Med.* (*Maywood*), 226:997-1002 (2001)). It has been shown that decreased actin and tubulin expression is an early adipogenic event that precedes overt changes in morphology and the expression of adipogenic markers (Spiegelman et al., *Cell*, 29:53-60 (1982)). Consistent with this finding, expression of several components involved in cytoskeletal organization and biogenesis, such as actin, myosin light chain, and troponins, was significantly decreased in IRS-1 KO preadipocytes (Table 1).

In addition, a switch of collagen gene expression occurs during early stage of white adipocyte differentiation (Weiner et al., *Biochemistry*, 28:4094-4099 (1989); Yi et al., *Exp. Mol. Med.*, 33:269-275 (2001)). Microarray analysis of the brown preadipocytes revealed that the levels of expression of procollagens type III α1 (Col3a1), Col4a1, Col4a2, Col6a1 and Col6a3, as well as tenascin XB were significantly decreased by 13-65% in IRS-1 KO cells, whereas Col7a1 and Laminin a4 were increased to about 2 times of the mean wild-type level (Table 1). Of these, Col4a2, Col6a1 and Col6a3 were significant down-progressors ($q_{down}$ for these genes between <0.001 and 0.003) (FIG. 2), and expression of Col6a1 was reversed by IRS-1 reconstitution in IRS-1 null cells (FIG. 3B). Furthermore, SPARC/osteonectin is a secreted protein involved in dynamic interaction between cell and matrix and has been found to be up-regulated in obesity (Tartare-Deckert et al., *J. Biol. Chem.*, 276:22231-22237 (2001)). Our microarray analysis showed a dramatic reduction of SPARC-like 1 (extraculluar matrix protein 2) in the IRS-1 null preadipocytes (Table 1) and it was also a significant down-progressor ($q_{down}$<0.001) (FIG. 2).

It has been shown that the matrix metalloproteinases (MMPs) are essential for ECM remodelling by degrading the structural matrix and/or adhesion receptors (Vu et al., *Genes. Dev.*, 14:2123-2133 (2000)). Two recent reports have shown the level of expression of several MMPs, including MMP-14, is increased in adipose tissue from obese mice as compared with lean mice (Chavey et al., *J. Biol. Chem.*, 278:11888-11896 (2003); Maquoi et al., *Diabetes*, 51:1093-1101 (2002)). We found that expression of MMP-14 was significantly decreased in IRS-1 KO preadipocytes (Table 1) and showed a trend to be a down-progressor, but did not quite reach our second criterion of significance.

Cell-cell communication is another important aspect of early adipogenesis. Inhibition of gap-junctional communication promotes adipocyte phenotype (Schiller et al., *J. Biol. Chem.*, 276:14133-14138 (2001)). In mature brown adipocytes, gap junctions are responsible for electrical coupling among adjacent adipocytes (Barbatelli et al., *Tissue Cell*, 26:667-676 (1994)). In IRS-1 KO preadipocytes the expression of gap junction membrane channel protein α1 (Gja1) was decreased to 25% of the mean wild-type levels and was also a significant down-progressor ($q_{down}$=0.004) (FIG. 2). In contrast, the expression of gap junction membrane channel protein β3 (Gjb3) was increased to 12 times the mean wild-type level (Table 1) and was a significant up-progressor ($q_{up}$=0.012) (FIG. 2). This overexpression of Gjb3 was reduced in IRS-1 reconstituted cells (FIG. 3A).

TABLE 1

Selective list of genes whose expression is significantly altered in IRS-1 KO brown preadipocytes

| Probe set | Gene Name | Symbol | $R^1$ | $p_{irs}^2$ | $q_{irs}^3$ | $q_{up}^4$ | $q_{down}^4$ |
|---|---|---|---|---|---|---|---|
| | Cytoskeleton Organization | | | | | | |
| 101028_i_at | Actin, alpha, cardiac | Actc1 | 0.05 | 0.0031 | 0.333 | ≧1.0 | 0.770 |
| 101029_f_at | Actin, alpha, cardiac | Actc1 | 0.41 | 0.0013 | 0.277 | 0.947 | 0.613 |
| 97904_at | Actin-related protein 3 homolog (yeast) | Actr3 | 1.29 | 0.0058 | 0.359 | 0.093 | ≧1.0 |
| 103430_at | Drebrin 1 | Dbn1 | 1.66 | 0.0031 | 0.333 | 0.493 | ≧1.0 |
| 95529_at | Drebrin-like | Dbnl | 2.37 | 0.0017 | 0.289 | 0.004 | ≧1.0 |
| 92541_at | Myosin, light polypeptide 1, alkali; atrial, embryonic | Myl1 | 0.11 | 0.0013 | 0.277 | 1.038 | 0.115 |
| 160487_at | Myosin, light polypeptide 4, alkali; atrial, embryonic | Myl4 | 0.29 | 0.0001 | 0.165 | 0.970 | 0.859 |
| 100828_at | Myosin, light polypeptide 4, alkali; atrial, embryonic | Myl4 | 0.39 | 0.0070 | 0.383 | 1.038 | 0.499 |
| 92541_at | Myosin light chain, alkali, fast skeletal muscle | Mylf | 0.11 | 0.0013 | 0.277 | ≧1.0 | 0.115 |
| 92881_at | Myosin light chain, phosphorylatable, fast skeletal muscle | Mylpf | 0.46 | 0.0066 | 0.381 | ≧1.0 | 0.308 |
| 101063_at | Troponin C, cardiac/slow skeletal | Tncc | 0.06 | 0.0066 | 0.381 | ≧1.0 | ≧1.0 |
| 98561_at | Troponin I, skeletal, slow 1 | Tnni1 | 0.19 | 0.0004 | 0.259 | ≧1.0 | 0.934 |
| 100593_at | Troponin T2, cardiac | Tnnt2 | 0.25 | 0.0027 | 0.321 | ≧1.0 | 0.622 |
| 92885_at | Troponin T3, skeletal, fast | Tnnt3 | 0.26 | 0.0013 | 0.277 | ≧1.0 | 0.407 |
| 96747_at | Ras homology gene family, member U (Wrch1) | Rhou | 9.31 | 0.0002 | 0.231 | 0.004* | ≧1.0 |
| 162011_f_at | Ras homology gene family, member U (Wrch1) | Rhou | 9.10 | 0.0080 | 0.397 | 0.012* | ≧1.0 |
| | Cell Adhesion | | | | | | |
| 104587_at | Laminin, alpha 4 | Lama4 | 1.97 | 0.0026 | 0.321 | 0.957 | ≧1.0 |
| 95016_at | Neuropilin | Nrp | 0.44 | 0.0075 | 0.392 | ≧1.0 | <0.001* |
| 98331_at | Procollagen, type III, alpha 1 | Col3a1 | 0.87 | 0.0076 | 0.393 | ≧1.0 | 0.382 |
| 101093_at | Procollagen, type IV, alpha 1 | Col4a1 | 0.40 | 0.0013 | 0.277 | ≧1.0 | 0.048 |
| 101039_at | Procollagen, type IV, alpha 2 | Col4a2 | 0.44 | 0.0001 | 0.138 | ≧1.0 | 0.003* |
| 162459_f_at | Procollagen, type VI, alpha 1 | Col6a1 | 0.44 | <0.0001 | 0.110 | ≧1.0 | 0.002* |
| 95493_at | Procollagen, type VI, alpha 1 | Col6a1 | 0.55 | <0.0001 | 0.132 | ≧1.0 | 0.003* |
| 101110_at | Procollagen, type VI, alpha 3 | Col6a3 | 0.37 | 0.0004 | 0.259 | ≧1.0 | <0.001* |
| 93383_at | Procollagen, type VII, alpha 1 | Col7a1 | 2.07 | 0.0086 | 0.413 | 0.010* | ≧1.0 |
| 161907_s_at | Tenascin XB | Tnxb | 0.35 | 0.0014 | 0.277 | ≧1.0 | 0.173 |
| 160319_at | SPARC-like 1 (mast9, hevin) | Sparcl1 | 0.09 | <0.0001 | 0.080 | ≧1.0 | <0.001* |
| 96272_at | Protein tyrosine phosphatase, receptor-type, F | Ptprf | 2.95 | 0.0024 | 0.321 | 0.013* | ≧1.0 |
| 97519_at | Secreted phosphoprotein 1 | Spp1 | 1.94 | 0.0066 | 0.381 | 0.180 | ≧1.0 |
| 102669_at | Sialoadhesin | Sn | 4.49 | 0.0061 | 0.366 | 0.723 | ≧1.0 |
| 92877_at | Transforming growth factor, beta induced. 68 kDa | Tgfbi | 0.60 | 0.0071 | 0.383 | ≧1.0 | 0.003* |
| 101637_at | CEA-related cell adhesion molecule 10 | Ceacam10 | 2.60 | 0.0066 | 0.381 | ≧1.0 | ≧1.0 |
| | ECM Proteolysis and Peptidolysis | | | | | | |
| 160118_at | Matrix metalloproteinase 14 (membrane-inserted) | Mmp14 | 0.71 | 0.0052 | 0.348 | ≧1.0 | 0.056 |
| | Cell Communication | | | | | | |
| 100064_f_at | Gap junction membrane channel protein alpha 1 | Gja1 | 0.23 | 0.0001 | 0.158 | ≧1.0 | 0.004* |
| 100065_r_at | Gap junction membrane channel protein alpha 1 | Gja1 | 0.23 | 0.0080 | 0.397 | ≧1.0 | 0.007* |
| 104232_at | Gap junction membrane channel protein beta 3 | Gjb3 | 12.32 | 0.0006 | 0.262 | 0.012* | ≧1.0 |
| 160857_at | Ephrin B2 | Efnb2 | 4.22 | 0.0023 | 0.321 | 0.004* | ≧1.0 |
| 101975_at | Preadipocyte factor-1 (Pref1) | Dlk1 | 7.79 | 0.0003 | 0.258 | 0.004* | ≧1.0 |
| | Wnt Signalling Pathway | | | | | | |
| 98862_at | Wingless related MMTV integration site 10a | Wnt10a | 2.37 | 0.0058 | 0.359 | 0.018* | ≧1.0 |
| 99390_at | Wingless-related MMTV integration site 5A | Wnt5a | 4.81 | 0.0002 | 0.251 | 0.732 | ≧1.0 |
| 97994_at | Transcription factor 7, T-cell specific | Tcf7 | 3.16 | 0.0006 | 0.262 | 0.004* | ≧1.0 |
| 93503_at | Secreted frizzled-related sequence protein 2 | Sfrp2 | 0.27 | 0.0003 | 0.251 | ≧1.0 | <0.001* |

TABLE 1-continued

Selective list of genes whose expression is significantly altered in IRS-1 KO brown preadipocytes

| Probe set | Gene Name | Symbol | $R^1$ | $p_{irs}{}^2$ | $q_{irs}{}^3$ | $q_{up}{}^4$ | $q_{down}{}^4$ |
|---|---|---|---|---|---|---|---|
| 96662_at | Phosphatidic acid phosphatase type 2B | Ppap2b | 0.51 | 0.0087 | 0.413 | ≧1.0 | <0.001* |
| 102044_at | WNT1 inducible signalling pathway protein 1 | Wisp1 | 3.20 | 0.0004 | 0.259 | 0.026* | ≧1.0 |
| 96747_at | Ras homolog gene family, member U (Wrch1) | Rhou | 9.31 | 0.0002 | 0.231 | 0.004* | ≧1.0 |
| 162011_f_at | Ras homolog gene family, member U (Wrch1) | Rhou | 9.10 | 0.0080 | 0.397 | 0.012* | ≧1.0 |
| Cell Cycle | | | | | | | |
| 94338_g_at | Growth arrest specific 2 | Gas2 | 0.31 | 0.0044 | 0.348 | ≧1.0 | 0.001* |
| 98531_g_at | Growth arrest specific 5 | Gas5 | 5.64 | 0.0008 | 0.269 | 0.004* | ≧1.0 |
| 98530_at | growth arrest specific 5 | Gas5 | 2.40 | 0.0017 | 0.285 | 0.248 | ≧1.0 |
| 101900_at | Cyclin-dependent kinase inhibitor 2B (p15, inhibits CDK4) | Cdkn2b | 1.40 | 0.0050 | 0.348 | 0.026* | ≧1.0 |
| 160638_at | Cyclin-dependent kinase inhibitor 2C (p18, inhibits CDK4) | Cdkn2c | 0.71 | 0.0002 | 0.231 | ≧1.0 | <0.001* |
| 96747_at | Ras homolog gene family, member U (Wrch1) | Rhou | 9.31 | 0.0002 | 0.231 | 0.004* | ≧1.0 |
| 162011_f_at | Ras homolog gene family, member U (Wrch1) | Rhou | 9.10 | 0.0080 | 0.397 | 0.012* | ≧1.0 |
| 101429_at | DNA-damage inducible transcript 3 | Ddit3 | 1.28 | 0.0006 | 0.262 | 0.398 | ≧1.0 |
| 102715_at | Nuclear receptor subfamily 2, group F, member 1 | Nr2f1 | 4.99 | 0.0045 | 0.348 | 0.060 | ≧1.0 |
| 100023_at | Myeloblastosis oncogene-like 2 | Mybl2 | 3.30 | 0.0005 | 0.260 | 0.672 | ≧1.0 |
| 92323_at | Mitogen-activated protein kinase 12 | Mapk12 | 2.21 | 0.0037 | 0.343 | 0.004* | ≧1.0 |
| 104097_at | Budding uninhibited by benzimidazoles 1 homolog (*S. cerevisiae*) | Bub1 | 1.65 | 0.0041 | 0.343 | ≧1.0 | ≧1.0 |
| 94932_at | Platelet derived growth factor, alpha | Pdgfa | 1.45 | 0.0077 | 0.393 | 0.757 | ≧1.0 |
| 97327_at | Flap structure specific endonuclease 1 | Fen1 | 1.39 | 0.0056 | 0.355 | 0.203 | ≧1.0 |
| 92348_at | Thyroid hormone receptor alpha | Thra | 0.74 | 0.0072 | 0.383 | ≧1.0 | 0.522 |
| Other Cell Growth and Maintenance | | | | | | | |
| 101059_at | Necdin | Ndn | 15.33 | 0.0001 | 0.152 | 0.004* | ≧1.0 |
| 104590_at | Myocyte enhancer factor 2C | Mef2c | 7.72 | 0.0028 | 0.322 | 0.077 | ≧1.0 |
| 103492_at | Carboxypeptidase X 1 (M14 family) | Cpxm1 | 6.44 | 0.0071 | 0.383 | 0.375 | ≧1.0 |
| 161028_at | Bone morphogenetic protein 6 | Bmp6 | 6.41 | 0.0096 | 0.432 | 0.024* | ≧1.0 |
| 161067_at | Mammalian homolog of *Drosophila* tribbles | Trib3 | 6.09 | 0.0017 | 0.289 | 0.004* | ≧1.0 |
| 100127_at | Cellular retinoic acid binding protein II | Crabp2 | 3.56 | 0.0053 | 0.348 | 0.004* | ≧1.0 |
| 100567_at | Fatty acid binding protein 4, adipocyte | Fabp4 | 0.46 | 0.0024 | 0.321 | ≧1.0 | 0.007* |
| 102044_at | WNT1 inducible signaling pathway protein 1 | Wisp1 | 3.20 | 0.0004 | 0.259 | 0.026* | ≧1.0 |
| 94367_at | Uridine monophosphate kinase | Umpk | 2.33 | 0.0026 | 0.321 | 0.006* | ≧1.0 |
| 94855_at | Prohibitin | Phb | 2.28 | 0.0023 | 0.321 | 0.781 | ≧1.0 |
| 92182_at | RUN and FYVE domain containing 1 | Rufy1 | 2.22 | 0.0070 | 0.383 | 0.108 | ≧1.0 |
| 104449_at | Glycine receptor, beta subunit | Glrb | 2.20 | 0.0041 | 0.343 | 0.019* | ≧1.0 |
| 97500_g_at | Four and a half LIM domains 1 | Fhl1 | 1.90 | 0.0072 | 0.383 | 1.038 | ≧1.0 |
| 93743_at | Heat shock factor binding protein 1 | Hsbp1 | 0.65 | 0.0048 | 0.348 | 1.038 | 0.027 |
| 100353_g_at | Heat shock protein 4 | Hspa4 | 1.42 | 0.0095 | 0.432 | 0.925 | ≧1.0 |
| 97914_at | Heat shock protein, A | Hspa9a | 1.86 | 0.0015 | 0.282 | 0.051 | ≧1.0 |
| 103215_g_at | Heat shock protein 2 | Hspb2 | 1.19 | 0.0000 | 0.133 | 0.160 | ≧1.0 |
| 161869_i_at | Heat shock protein 1, alpha | Hspca | 2.24 | 0.0050 | 0.348 | ≧1.0 | ≧1.0 |
| 160832_at | Low density lipoprotein receptor | Ldlr | 1.79 | 0.0027 | 0.321 | 0.715 | ≧1.0 |
| 93700_at | ADP-ribosylation factor 3 | Arf3 | 1.24 | 0.0019 | 0.303 | 0.677 | ≧1.0 |
| 95686_at | RAB14, member RAS oncogene family | Rab14 | 0.61 | 0.0011 | 0.277 | 1.038 | 0.047 |
| 160868_at | RAB3B, member RAS oncogene family | Rab3b | 0.14 | 0.0100 | 0.432 | 1.038 | 0.468 |
| 104108_at | Rab6 interacting protein 1 | Rab6ip1 | 0.88 | 0.0081 | 0.399 | 1.038 | 0.550 |
| 95516_at | RAB9, member RAS oncogene family | Rab9 | 0.46 | 0.0039 | 0.343 | 1.038 | <0.001* |
| 102878_at | RAD52 homolog (*S. cerevisiae*) | Rad52 | 0.75 | 0.0009 | 0.271 | 1.038 | 0.991 |
| 93895_s_at | Inositol 1,4,5-triphosphate receptor 1 | Itpr1 | 0.49 | 0.0040 | 0.343 | ≧1.0 | 0.426 |
| 95546_g_at | Insulin-like growth factor 1 | Igf1 | 1.44 | 0.0100 | 0.432 | 0.949 | 1.070 |
| 101571_g_at | Insulin-likegrowth factor binding protein 4 | Igfbp4 | 0.46 | 0.0049 | 0.348 | ≧1.0 | 0.348 |
| 101593_at | Cysteine rich protein 2 | Crip2 | 0.43 | 0.0049 | 0.348 | ≧1.0 | 0.999 |
| 94794_at | Ferritin heavy chain | Fth | 0.74 | 0.0041 | 0.343 | ≧1.0 | 0.235 |
| 101991_at | Flavin containing monooxygenase 1 | Fmo1 | 0.30 | <0.0001 | 0.130 | ≧1.0 | 0.003* |
| 94367_at | Uridine monophosphate kinase | Umpk | 2.33 | 0.0026 | 0.321 | 0.006* | ≧1.0 |
| 100697_at | Paired box gene 3 | Pax3 | 0.47 | 0.0030 | 0.333 | ≧1.0 | 0.007* |
| 98144_f_at | Sarcoma amplified sequence | Sas | 0.60 | 0.0025 | 0.321 | ≧1.0 | ≧1.0 |

[1] Ratio of mean expression level in IRS-1 KO cells over mean expression level in WT littermate cells.
[2] $p_{irs}$ were calculated by using Student's t-test with unpaired values, with Welch correction for unequal variance.
[3] $q_{irs}$ values are the minimum ratio of number of false positives we would expect over the total number of significant genes if the gene and those with lower $p_{irs}$ are called significant, calculated as described by Storey and Tibshirani, supra.
[4] $q_{up}$ and $q_{down}$ are similar q-values for the assessment of gene-specific false discovery rates with regards to the Bartholomew's test of homogeneity for ordered alternatives. See Methods for details.
*Genes that show a significant up- or down-progression, as defined as a $q_{up}$ or $q_{down}$ <0.03.

Example 3

Coordinated Chances in Expression of Genes of Wnt Signalling Pathway in Cells with Impaired Adipocyte Differentiation The Wnt signalling pathway has previously been shown to exert an inhibitory function in the differentiation of 3T3-L1 preadipocytes (Ross et al., *Science*, 289:950-953 (2000)). Recently, Kang et al. reported that activation of Wnt signalling early in differentiation blocked brown adipogenesis, while activating this pathway in mature brown adipocyte promoted conversion to white adipocytes (Kang et al., *Mol. Cell. Biol.*, 25:1272-1282 (2005)). Microarray analysis revealed the levels of expression of several members of the Wnt signalling pathway were coordinately altered in the IRS-1 KO cells (Table 1). These included significantly increased expression of Wnt10a, Wnt5a, and the transcription factor Tcf7. Expression of Wnt4 and Wnt6 was also increased in IRS-1 KO cells to 1.24 and 2.46 times the mean WT level, but did not quite meet our criteria of significance with $p_{irs}$=0.0197 and 0.0165, respectively. Among these genes, Wnt10a and Tcf7 also showed significant up-progression in cells with decreasing abilities in differentiation ($q_{up}$=0.018 and 0.004, respectively) (FIG. 2). Interestingly, expression of the naturally occurring Wnt antagonist Sfrp2 (Kawano et al., *J. Cell. Sci.*, 116:2627-2634 (2003)) was significantly decreased in the IRS-1 deficient cells to 27% of the mean WT level and was also a significant down-progressor ($q_{down}$<0.001) (FIG. 2). Moreover, expression of phosphatidic acid phosphatase type 2B (Ppap2b, also known as Lpp3) which was previously shown to regulate Wnt signalling by inhibiting β-catenin-mediated TCF transcription (Escalante-Alcalde et al., *Development*, 130:4623-4637 (2003)), was significantly decreased in IRS-1 KO cells by half of the mean WT level (Table 1) and was a down-progressor ($q_{down}$<0.001) (FIG. 2). Associated with and probably as a result of these changes, two Wnt-inducible genes, Wisp1 and Rhou (also known as Wrch1), increased in expression to 3.2 and 9.3 times the mean WT level and were significant up-progressors by Bartholemew's test ($q_{up}$=0.026 and 0.004, respectively). Taken together, these changes in gene expression provide strong evidence for enhanced Wnt signalling in the IRS-1 KO cells and a coordinated regulation of multiple members of this pathway by the IRS system in brown adipocyte differentiation.

Example 4

Expression of Other Regulators of Preadipocyte-Adipocytes Transition is Altered in IRS KO Cells Pref-1 is a member of the EGF-like transmembrane protein family. It is highly expressed in preadipocytes and undetectable in mature fat cells. Adipocyte differentiation is inhibited in 3T3-L1 cells that constitutively express Pref-1 (Smas et al., *Cell*, 73:725-734 (1993)). Consistent with these findings, expression of Pref-1 in IRS-1 KO brown preadipocyte was increased to 7.8 times the mean wild-type level (Table 1) and was a significant up-progressor ($q_{up}$=0.004) (FIG. 2). This overexpression was reduced in IRS-1 reconstituted cells (FIG. 3A).

One transcription factor whose expression pattern seems to conflict with the observation in white adipogenesis is Gata3. Gata3 has been previously shown to inhibit white adipocyte differentiation (Tong et al., *Science*, 290:134-138 (2000)), whereas we found that the expression of Gata3 was progressively lower in genotypes of brown preadipocytes with defects in differentiation ($q_{down}$=0.025) (data not shown). Whether or not this represents a molecular control that distinguishes white vs. brown fat differentiation or some other aspect of regulation of this transcription factor is unclear.

Example 5

Figure 5B:
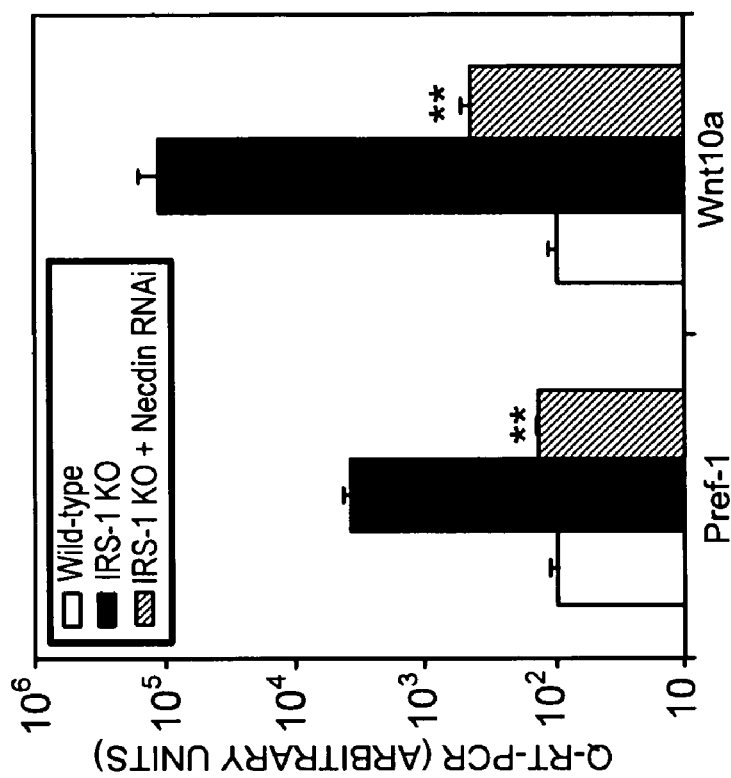
FIGS. 5B-C are bar grahs illustrating the results of quantitative RT-PCR analysis for Pref-1 (5B), Wnt10a (5B), PGC-1α (5C) and PPARγ (5C) using total RNAs isolated from preadipocytes of WT, IRS-1 KO and IRS-1 KO stably expressing necdin RNAi. Data are presented as mean±SEM. Asterisks depict statistically significant differences between IRS-1 KO and IRS-1 KO+necdin RNAi by unpaired, unequal t test (*=P<0.05, =P<0.01, *=P<0.001).
Figure 5A:
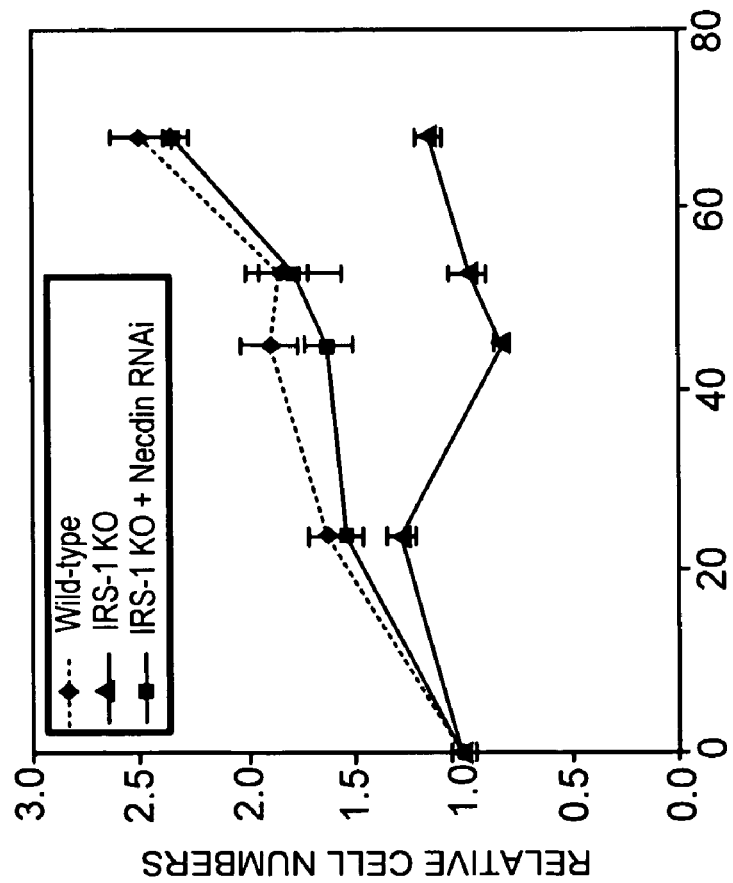
FIG. 5A is a line graph illustrating that Necdin RNAi restores mitotic clonal expansion. WT, IRS-1 KO and IRS-1 KO cells stably expressing necdin RNAi were plated at density $1.5 \times 10^5$ per well in 12-well plate and grown to confluence. Cells were then induced to differentiation using the induction cocktail described in Methods (O hour). After 48 hours of induction period, cells were changed back to regular medium supplemented with 20 nM insulin and 1 nM T3. At the time indicated, cells were trypsinized and counted in a hemocytometer. Data are plotted as relative cell number at each time point to those at 0 hour for each cell line. Error bars represent standard error of mean from triplicate wells. The results are representative of two independent experiments.
Figure 5D:
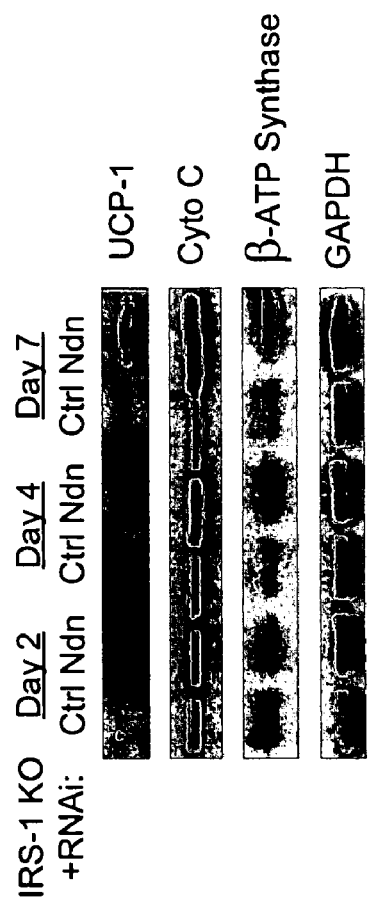
FIG. 5D shows the results of Western blotting analysis of mitochondrial proteins UCP-1, ubiquinol-cytochrome c oxidoreductase (Cyto C) and the β subunit of ATP synthase in IRS-1 KO cells stably expressing an unrelated control RNAi or necdin RNAi at days 2, 4, and 7 of differentiation. Blots were stripped and reprobed with GAPDH to normalize for variation in loading and transfer of proteins.
Figure 5C:
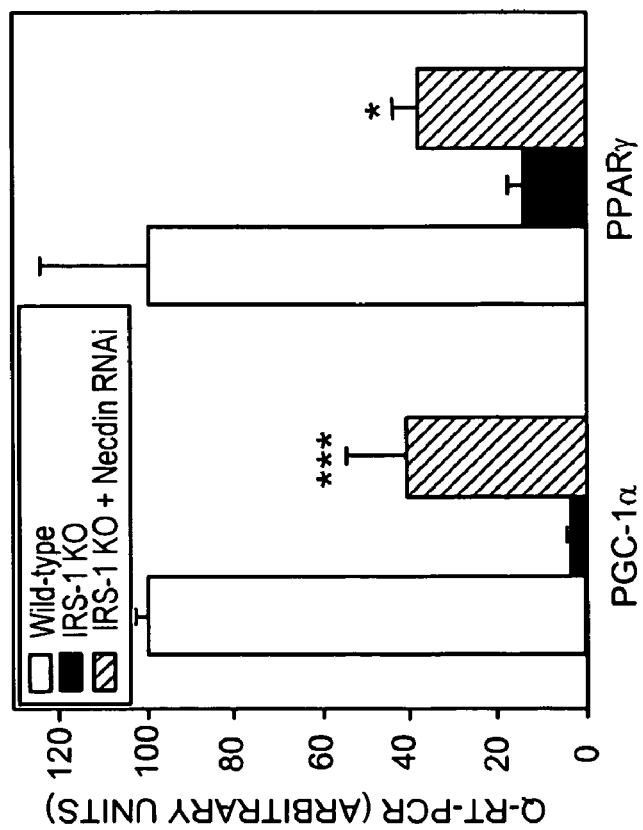

Expression of Genes Involved in Growth Arrest/Cell Cycle Controls is Altered in Cells with Impaired Adipocyte Differentiation Preadipocytes have to pass through stages of growth arrest and mitotic clonal expansion before becoming committed to terminal differentiation (Gregoire et al., *Physiol. Rev.*, 78:783-809 (1998)). IRS-1 KO cells displayed a marked defect in mitotic clonal expansion following treatment with the induction cocktail (FIG. 5C). Not surprisingly, expression of many genes involved in the regulation of cell cycle and cell growth was altered in the IRS KO cells (Table 1). In particular, expression of the growth arrest specific genes, Gas2 and Gas5, as well as two CDK4 inhibitors, Cdkn2b and Cdkn2c, were significantly altered between WT and IRS-1 KO brown preadipocytes, suggesting a dynamic change in the control of the exit and re-entry of cell cycle regulated by insulin or IGF-1 in adipogenesis (Table 1). Among these genes, Gas2 and Cdkn2c were significant down-progressor ($q_{down}$≦0.001); and Gas5 and Cdkn2b were significant up-progressors ($q_{up}$=0.004 and 0.026, respectively). Furthermore, myocyte enhancer factor 2C (Mef2c), a transcription factor that regulates different aspects of cell differentiation and death (McKinsey et al., *Trends Biochem. Sci.*, 27:40-47 (2002)), was increased in IRS-1 KO brown preadipocytes to 7.7 times the mean wild-type level. Interestingly, expression of Trib3 (also known as TRB-3) was progressively increased in preadipocytes with increasing defects in differentiation ($q_{up}$=0.004) (FIGS. 1 and 2), implicating a potential role of this protein in regulation of brown adipogenesis.

Trib3 met two statistical criteria: Criterion 1, expression was significantly different between IRS-1 KO and WT littermate cells in a Student's t-test with unpaired values and the Welch correction for unequal variance with $p_{irs}$<0.01; Criterion 2, this gene showed a significant upward ordering of mean basal expression level across the genotypes. Each gene was evaluated for differential expression between IRS-1 KO and WT littermate cells, and as an up- or down-progressor.

Trib3 is the mammalian homolog of *Drosophila* gene tribbles that inhibits mitosis in early development (Grosshans et al., *Cell*, 101:523-531 (2000); Mata et al., *Cell*, 101:511-522 (2000)), and has been shown to act as an inhibitor of insulin signalling by directly binding to Akt (Du et al., *Science*, 300:1574-1577 (2003)). As noted above, Rhou and Wisp 1, two genes that are induced by Wnt signalling pathway and previously known to promote cell growth (Tao et al., *Genes. Dev.*, 15:1796-1807 (2001); Pennica et al., *Proc. Natl. Acad. Sci. USA*, 95:14717-14722 (1998)), were both increased in expression in IRS-1 KO cells. Taken together, these data suggest a potential role for these proteins in the regulation of adipogenesis involving the proliferative phase of preadipocyte and/or the post-mitotic clonal expansion stage of committed cells of adipogenesis.

Example 6

IRS-1 Reconstitution Reverses Most Gene Expression

To confirm that the changes in gene expression were only due to the lack of IRS-1, we characterized IRS-1 KO cells in which IRS-1 was reintroduced by stable retroviral infection. We have previously shown that IRS-1 reconstituted cells express about 65% of the level of IRS-1 protein as seen in the WT cells (Tseng et al., *J. Biol. Chem.*, 277:31601-31611 (2002)) and exhibit a fully differentiated phenotype (Fasshauer et al., *Mol. Cell. Biol.*, 21:319-329 (2001)). The genes over-expressed in IRS-1 KO cells, such as Pref-1, Gjb3, Trib3, Mef2c, Wnt6, Wnt10a and necdin, were significantly reduced by IRS-1 re-expression (FIG. 3A). Likewise, the reduced levels of expression of Col6a1, Gata3, Fabp4 and Sfrp2 were reversed in the reconstituted cells (FIG. 3B). Interestingly, not all the changes in gene expression in the IRS-1 KO cells could be reversed by IRS-1 re-expression at this level. For example, IRS-1 reconstitution failed to reverse the elevated expression of Wnt5a, Tcf7 and Wisp1 (FIG. 3A). Whether this reflects the fact that the level of IRS-1 re-expression achieved by retroviral infection is not sufficient to reverse some gene expression or represents epigenetic alterations, such as changes in DNA methylation (Jaenisch et al., *Nat. Genet.*, 33 Suppl.:245-254 (2003)), in the IRS-1 KO cells is unclear and a subject for further study.

Example 7

Concordant Changes in Gene Expression in Adipose Tissues In Vivo

Figure 3C:
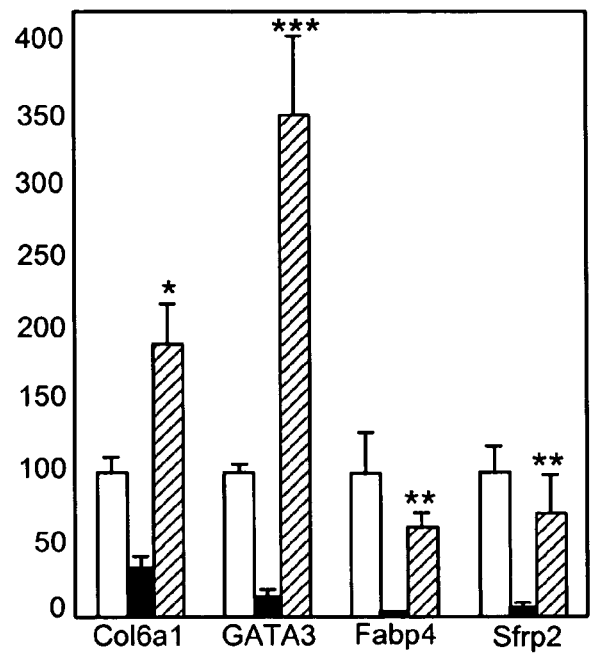
Figure 3D:
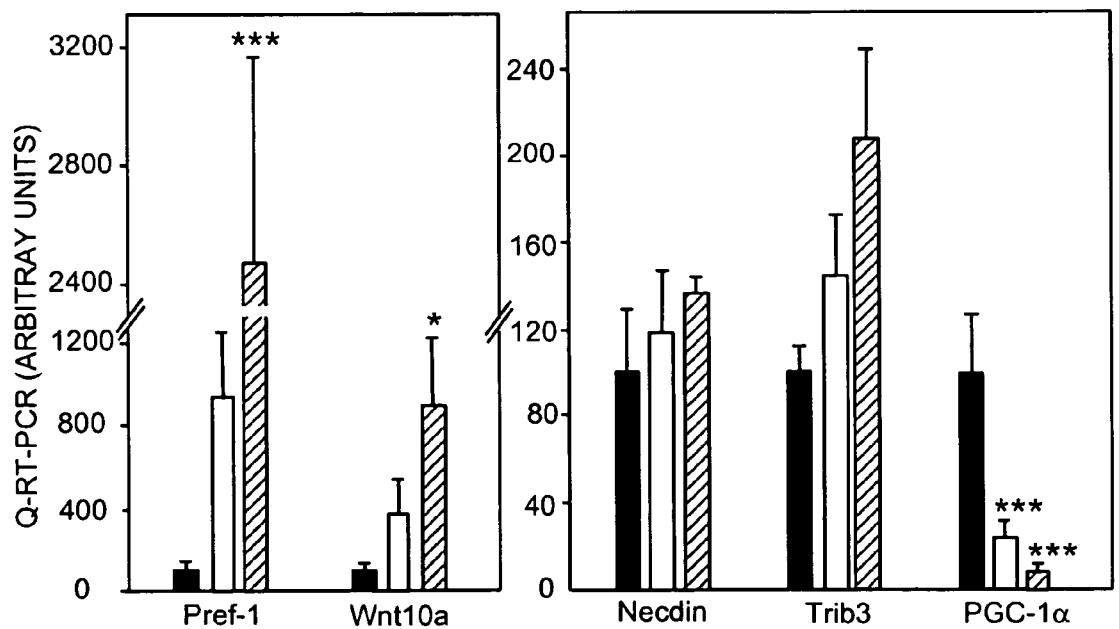
Figure 3E:
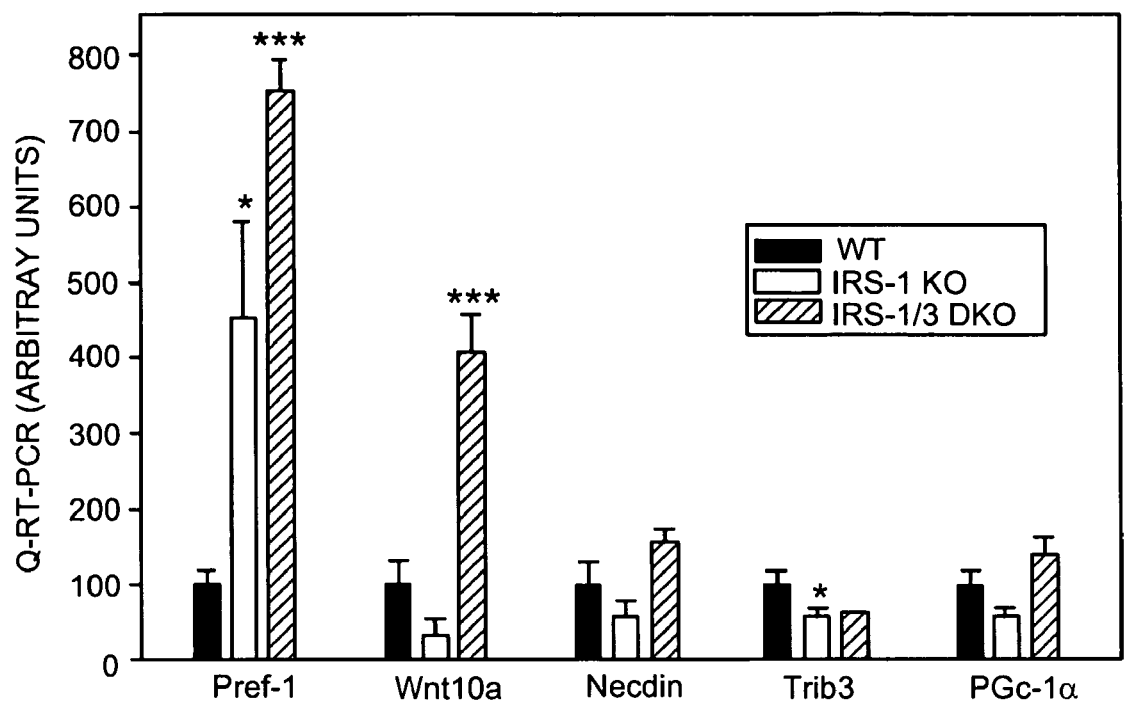

To determine the changes in gene expression in cultured preadipocytes described above were applicable to the in vivo mechanisms of adipogenesis, we measured gene expression in brown and white adipose tissues isolated from WT, IRS-1 KO and IRS-1/3 double KO (DKO) mice by quantitative RT-PCR (FIGS. 3C and D). The IRS-1 KO mice exhibit embryonic and postnatal growth retardation (Araki et al., *Nature*, 372:186-190 (1994); Tamemoto et al., *Nature*, 372:182-186 (1994)). As a result, these mice have general reduction in size of all organs and tissues, including both brown and white adipose tissues. More interestingly, although IRS-3 KO mice are normal in growth and glucose metabolism (Liu et al., *J. Biol. Chem.*, 274:18093-18099 (1999)), the IRS-1/3 DKO mice exhibit marked lipoatrophy with severe insulin resistance (Laustsen et al., *Genes. Dev.*, 16:3213-3222 (2002)). Consistent with these phenotypes, expression of Pref-1 and Wnt10a was progressively increased in brown fat taken from mice with increasing defects in the development of adipose tissues. Furthermore, expression of Pref-1 also showed a progressive increase in white adipose tissue of the KO and DKO mice. In addition, expression of PGC-1α in brown adipose tissue was significantly and progressively decreased in mice with increasing deficiency in the development of mature adipose tissues. Necdin and Trib3 also exhibited trends toward increased expression in brown adipose tissue, but did not reach statistical significance. Taken together, these data reveal many of the changes in gene expression observed in brown preadipocytes in culture derived from mice with defects in insulin signalling also occurred in brown adipose tissues in vivo in the presence of similar genetic defects.

However, since the fat tissue contains several other components besides adipocytes, including preadipocytes, endothelial cells, smooth muscle cells, fibroblast, mast cells, and macrophages, the changes of gene expression observed here reflect an overall change of gene expression from all cell type. We cannot conclude whether gene expression is changed in mature adipocytes from IRS-1 KO or IRS-1/3 DKO mice. To ultimately address this question would require separation of all of the cell populations in the various fat pads and an analysis of gene expression in each of the different cell types of adipose tissue, especially the preadipocytes. Unfortunately, at present there are no good surface markers of these cells to allow separation. In addition, the exact pattern of gene expression in vivo may be different from that in vitro since the mixture of growth factors, matrix components, etc. is much more limiting in vitro. This allows identification of specific "rate limiting" factors which may be partially masked in vivo.

Example 8

Role of Necdin in Brown Preadipocyte Differentiation

Necdin is one of a cluster of genes deleted in some patients with the Prader-Willi syndrome (PWS), a neurodevelopmental disorder with major symptoms such as feeding problems, gross obesity and hypogonadism (Goldstone, *Trends Endocrinol. Metab.*, 15:12-20 (2004)). Necdin functions as a growth suppressor in postmitotic neurons (Taniura et al., *J. Biol. Chem.*, 273:720-728 (1998)), and promotes differentiation and survival of neurons (Kobayashi et al., *J. Biol. Chem.*, 277:42128-42135 (2002)). Necdin also interacts with viral proteins and transcription factors of the E2F family. These characteristics resemble those of the pRb protein.

Figure 4A:
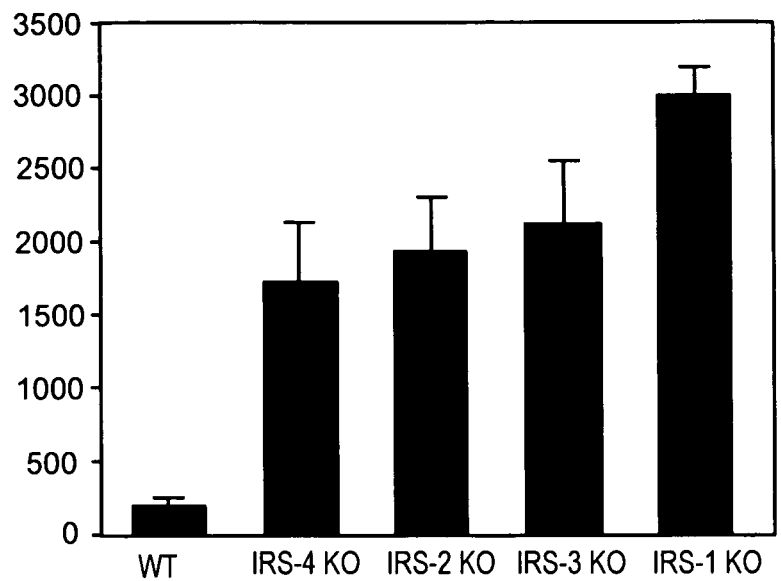
FIG. 4A is a bar graph illustrating that expression of necdin was progressively increased in preadipocytes with increasing defects in differentiation.
Figure 4B:
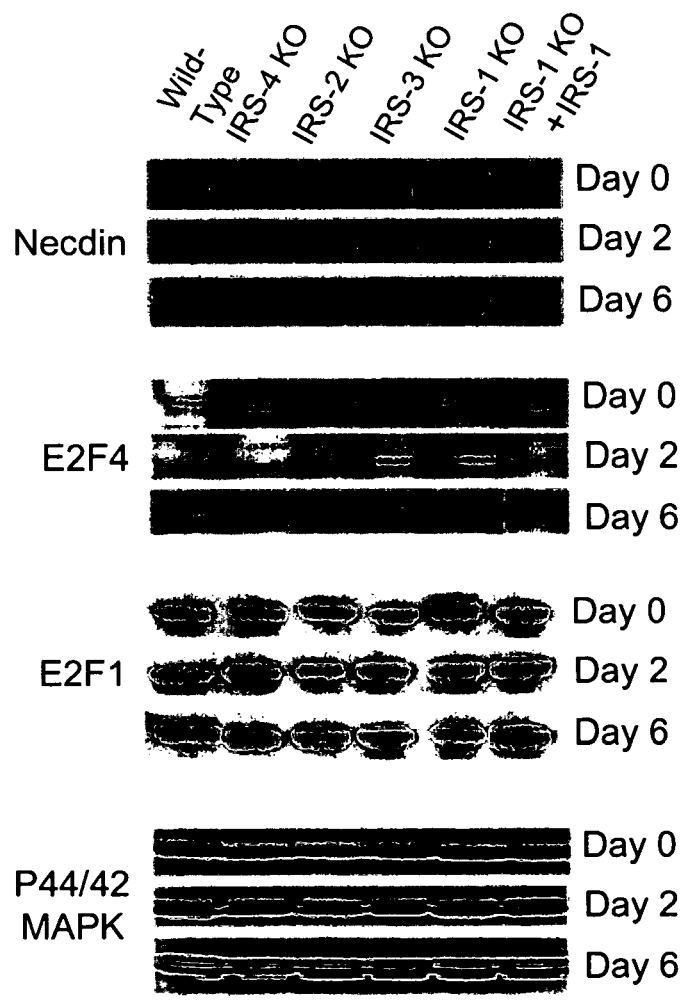
FIG. 4B is a set of 12 panels showing Western blots of protein expression of necdin (top trio), E2F4 (next trio) and E2F1 (third trio) in WT, different IRS KO and IRS-1 reconstituted cells at day 0, day 2 and day 6 of differentiation. The bottom trio shows similar levels of p44/42 MAP kinase expression among different samples to ensure equal loadings.

In IRS-1 KO brown preadipocytes, expression of necdin mRNA and protein was significantly and progressively increased in cells with decreasing ability in differentiation ($q_{up}$=0.004) (FIGS. 2, 4A and 4B). IRS-1 reconstitution of the IRS-1 KO cells significantly reduced this high level of necdin mRNA and protein as it restored the ability of these cells to differentiate (Fasshauer et al., *Mol. Cell. Biol.*, 21:319-329 (2001)) (FIGS. 3A and 4B).

Since necdin has been shown to interact with E2F4 and E2F1 in control of gene transcription (Kobayashi et al., *J. Biol. Chem.*, 277:42128-42135 (2002)), we first examined the expression of E2F4 and E2F1 proteins in WT and IRS KO cells during differentiation (FIG. 4B). E2F4 was expressed at similar levels in WT and all IRS KO cells at day 0, and this expression was almost completely diminished at days 2 and 6 in the cells that could differentiate (i.e., WT, IRS-4 KO, and IRS-2 KO). By contrast, E2F4 protein levels remained high in cells with impaired ability in differentiation (i.e., IRS-1 KO and IRS-3 KO cells). E2F1 protein, on the other hand, was present at similar levels in all cells throughout the whole differentiation course.

Figure 4C:
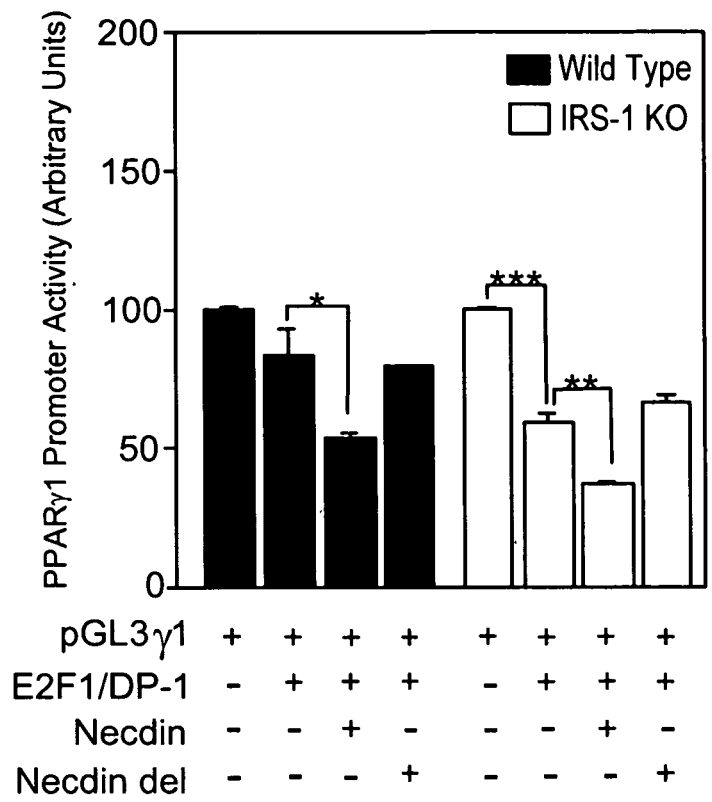
FIGS. 4C-D are bar graphs illustrating the regulation of PPARγ1 promoter activities by interactions of necdin and E2F4 (4C) or E2F1 (4D) in WT and IRS-1 KO brown preadipocytes. Relative luciferase activities were measured after transfection with reporter gene construct pGL3γ1 and combinations of expression vectors for DP-1, E2F4, E2F1, necdin, and a truncated necdin mutant as indicated. Data are presented as mean±SEM. Significance was determined by unpaired, unequal t test with *=P<0.05, =P <0.01, *=P<0.001. Western blotting analysis of E2F4 and E2F1 was used to ensure similar levels of expression of these proteins in different transfection.
Figure 4D:
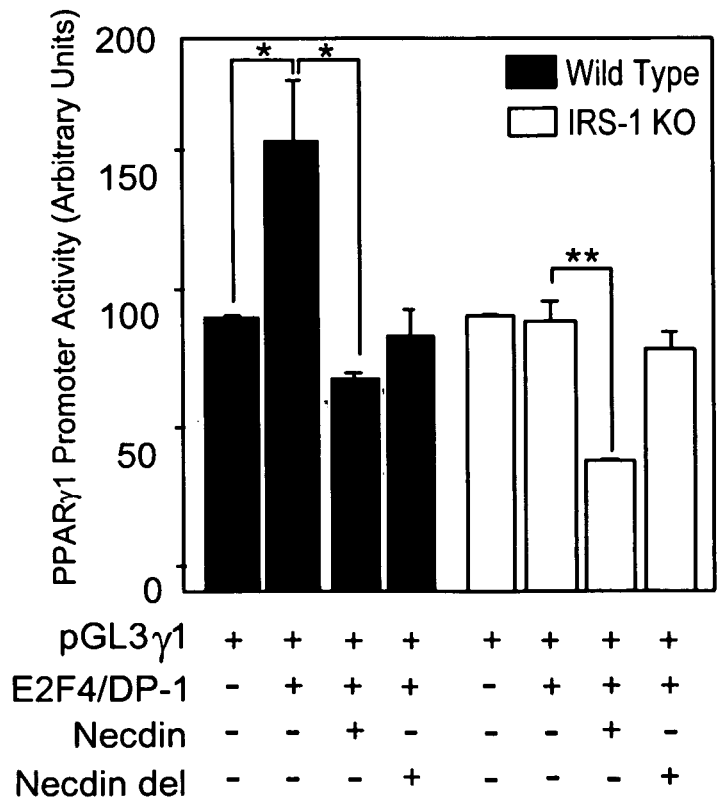

To determine the molecular mechanisms by which necdin might regulate brown fat differentiation, we co-transfected WT and IRS-1 KO cells with expression constructs of E2F4, E2F1, necdin, a truncated mutant of necdin lacking the E2F-interacting domain (Kobayashi et al., *J. Biol. Chem.*, 277:42128-42135 (2002)) together with a luciferase reporter gene construct containing 3000 bp of regulatory sequence of human PPARγ1 gene (Fajas et al., *Dev. Cell*, 3:39-49 (2002)) (FIGS. 4C and 4D). In WT cells, the E2F4/DP-1 heterodimeric complex was able to stimulate PPARγ1 promoter activity to 2 times the control level. This was significantly abolished by expression of full-length necdin.

The decrease in reporter gene activity seen in WT cells co-transfected with the truncated necdin and E2F4/DP-1 as compared to that induced by E2F4/DP-1 suggest additional E2F4-interacting sites may be present in the N-terminal region of necdin. Necdin by itself did not have any effect on regulating PPARγ promoter activity. The stimulatory effect of E2F4 on PPARγ1 promoter activity was blunted in the IRS-1

KO cells, presumably due to the high level of necdin protein present in these cells. Forced expression of full-length necdin, but not the deletion mutant of necdin, in the IRS-1 KO further reduced PPARγ1 promoter activity.

In contrast to E2F4, the E2F1/DP-1 did not have any effect on PPARγ1 transcription in the WT cells. Overexpression of full-length, but not the truncated mutant of necdin, in these cells decreased PPARγ1 promoter activity, suggesting that this inhibitory effect was mediated via the C-terminal region of necdin. This repressive effect of necdin on PPARγ1 gene transcription was further demonstrated in the IRS-1 KO cells, since E2F1/DP-1 complex significantly reduced PPARγ1 promoter activity in these cells with high level of necdin protein. Co-transfection of necdin together with the E2F1 and DP-1 constructs further decreased the reporter gene activity. These data suggest that in brown preadipocytes necdin inhibits PPARγ1 gene expression via interaction with the E2Fs, providing a potential molecular mechanism by which it regulates adipogenesis.

Interestingly, stable overexpression of E2F4 protein in the IRS-1 KO cells resulted in a marked enhancement of differentiation, confirming a stimulatory effect of E2F4 on brown adipocyte differentiation.

Example 9

Knocking Down Necdin Expression Restores Differentiation, Mitotic Clonal Expansion, Gene Expression and Characteristics of Brown Adipocytes To further examine the role of necdin in regulation of brown adipocyte differentiation, we knocked down the high level of necdin expression in IRS-1 KO cells using RNA interference. Since pilot experiments using transient transfection to deliver necdin siRNA resulted in only modest changes in necdin protein expression and differentiation in IRS-1 KO cells, to achieve maximum knock down effect, we isolated clones that were stably transfected with a construct containing inhibitory short hairpin RNA (RNAi) targeting necdin. Western blotting analysis of necdin and Pref-1 in preadipocytes of WT, IRS-1 KO and IRS-1 KO stably expressing necdin RNAi showed that this treatment resulted in a nearly 90% reduction of necdin protein expression, and Oil Red O staining of WT, IRS-1 KO and IRS-1 KO cells stably expressing necdin RNAi at day 6 of differentiation illustrated about 80% recovery in differentiation compared to WT.

In addition, the effect of down-regulation of necdin in IRS-1 KO cells on mitotic clonal expansion was evaluated in WT, IRS-1 KO and IRS-1 KO cells stably expressing necdin RNAi. Cells were plated at density $1.5 \times 10^5$ per well in 12-well plate and grown to confluence. Cells were then induced to differentiation using the induction cocktail described in Methods (O hour). After 48 hours of induction period, cells were changed back to regular medium supplemented with 20 nM insulin and 1 nM T3. At the time indicated, cells were trypsinized and counted in a hemocytometer. The results demonstrated that down-regulation of necdin in IRS-1 KO cells reversed the defect in mitotic clonal expansion (FIG. 5A) and almost completely suppressed the expression of Pref-1 and Wnt10a, two inhibitors of early adipogenesis as described above (FIG. 5B).

Western blotting analysis confirmed the reduction of Pref-1 protein in IRS-1 KO preadipocytes expressing necdin RNAi. Furthermore, the markedly decreased levels of PGC-1α and PPARγ mRNA observed in the IRS-1 KO preadipocytes were partially restored by knock down necdin (FIG. 5C). This led to a profound restoration in protein expression of brown fat-specific marker UCP-1 and mitochondrial proteins ubiquinol-cytochrome c oxidoreductase and the β subunit of ATP synthase (FIG. 5D). IRS-1 KO cells stably expressing an unrelated RNAi showed no effect on differentiation, mRNA and protein expression, and cell growth. These data suggest that down-regulation of necdin expression in IRS-1 KO cells not only reverses differentiation but also restores characteristics of mature brown adipocytes.

Figure 9A:
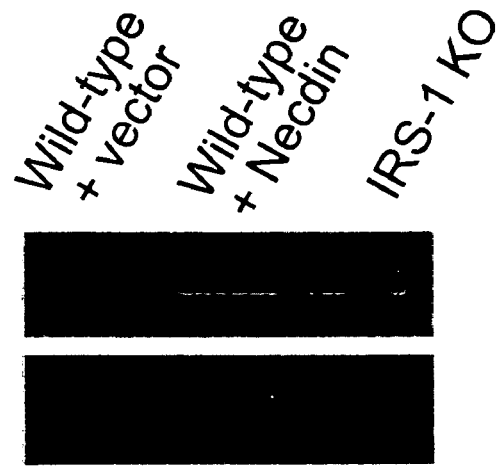
FIG. 9A is a Western blot analysis of necdin in preadipocytes of WT overexpressing necdin or empty vector, and IRS-1 KO cells.
Figure 9B:
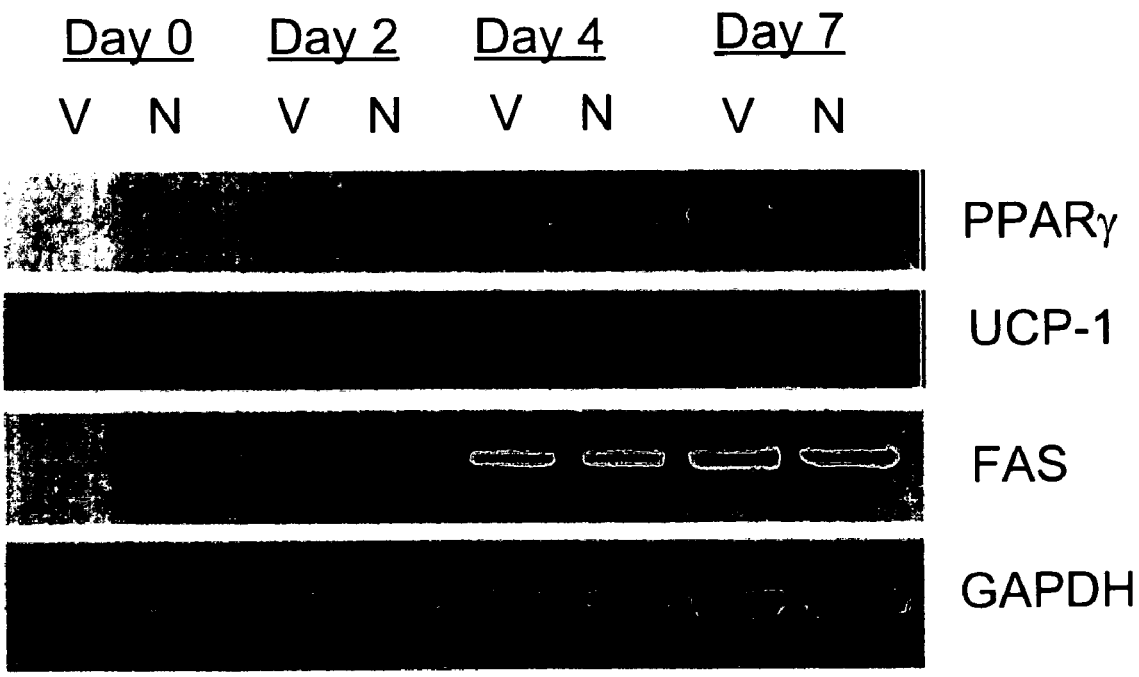
FIG. 9B is a Western blot analysis of PPARγ, UCP-1 and fatty acid synthase (FAS) WT overexpressing empty vector [V] or necdin [N] at day 0, 2, 4, and 7 of differentiation. The blots in 9A and 9B were stripped and reprobed with GAPDH to normalize for variation in loading and transfer of proteins. The results are representative of two independent experiments.

We also generated WT brown preadipocytes overexpressing necdin using retroviral-mediated gene transfer (FIG. 9). Although forcing necdin overexpression in these already committed brown preadipocytes did not block lipid accumulation, there was a decrease in protein expression of adipogenic marker PPARγ and brown fat specific marker UCP-1. These data suggest that either additional factors produced by the altered insulin signalling must interact with necdin to produce the full phenotype of inhibition of adipogenesis in the IRS-1 KO cells, or that necdin overexpression must act in an even earlier state, i.e., prior to preadipocyte determination.

Example 10

CREB as a Potential Transcription Factor That Drives Multiple Genes Involved in Adipogenesis One of the challenging issues in many studies of expression profiling is to identify 20' the transcription factors that drive the changes in gene expression observed in the microarray studies. To this end, we examined the 2 Kb promoter region of the genes that were regulated in the IRS-1 KO cells using the SRMS (Silico Informatics Systems, Santa Clara, Calif.) and TRANSFAC programs. One of the motifs revealed by this approach in many of the up- and down-regulated genes was the response element for cAMP response element binding protein (CREB) (data not shown). Previously, we found that phosphorylation of CREB on Ser133 was rapidly induced by IGF-1 or insulin stimulation in the WT preadipocytes, and that stimulation was markedly diminished in the IRS-1-dificient cells (Tseng et al., *J. Biol. Chem.*, 277:31601-31611 (2002)). In the present study we found that the levels of IGF-1-stimulated CREB phosphorylation at Ser 133 were progressively decreased in the cells with increasing defects in differentiation (FIGS. 6A and 6B). Similar patterns were observed following insulin treatment (data not shown). Interestingly, forskolin, a potent activator of cAMP-dependent responses, also failed to stimulate CREB phosphorylation in IRS-1 KO cells (FIG. 6C). IRS-1 re-expression in these cells not only restored CREB phosphorylation in response to acute IGF-1 stimulation (Tseng et al., *J. Biol. Chem.*, 277:31601-31611 (2002)) but also reversed cAMP responsiveness (data not shown). These data suggest a common pathway that is utilized by both IGF-1/insulin and forskolin is defective in the IRS-1 KO cells.

To determine if CREB might be the link between the insulin/IRS pathway and regulation of gene expression in brown preadipocytes, we stably expressed a constitutively active (CA) form of CREB in IRS-1 KO preadipocytes and examined whether this protein was able to reverse gene expression and/or differentiation. As shown in FIG. 6D, CA-CREB significantly decreased the high levels of expression of Wnt10a, necdin and Gjb3. Interestingly, however, CA-CREB was not able to reverse Pref-1 gene expression, although there was a slight increase in lipid accumulation in these cells. Thus, insulin-induced CREB activation appears to be required for some of the changes in gene expression involved in adipocyte differentiation, but CREB alone is not sufficient to trigger the whole differentiation process.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of promoting brown adipocyte differentiation, the method comprising contacting a preadipocyte or a white adipocyte with a small interfering RNA (siRNA) that binds specifically to an mRNA encoding Necdin, wherein the mRNA comprises SEQ ID NO:2, wherein the siRNA selectively inhibits Necdin expression in an amount sufficient to increase Uncoupling Protein-1 (UCP-1) expression in the preadipocyte or white adipocyte, thereby promoting brown adipocyte differentiation.

2. The method of claim 1, wherein the preadipocyte comprises a brown preadipocyte.

3. The method of claim 1, wherein the preadipocyte comprises a white preadipocyte.

4. The method of claim 1, further comprising contacting the preadipocyte or white adipocyte with another agent selected from the group consisting of bone morphogenetic protein 2 (BMP-2), bone morphogenetic protein 4 (BMP-4), bone morphogenetic protein 5 (BMP-5), bone morphogenetic protein 6 (BMP-6), or bone morphogenetic protein 7 (BMP-7), bone morphogenetic protein 1 (BMP-1), bone morphogenetic protein 3 (BMP-3), peroxisome proliferator-activated receptor gamma (PPARγ), Retinoid X receptor, alpha (RxRα), insulin, T3, a thiazolidinedione (TZD), vitamin A, retinoic acid, insulin, glucocorticoid or agonist thereof, Wnt, insulin-like growth factor (IGF), epidermal growth factor (EGF), fibroblast growth factor (FGF), transforming growth factor alpha (TGFα), TGFβ, tumor necrosis factor alpha (TNFα), Macrophage colony stimulating factor (MCSF), vascular endothelial growth factor (VEGF) and Platelet Derived Growth Factor (PDGF).

5. The method of claim 1, wherein the preadipocyte or white adipocyte is in culture.

6. The method of claim 1, wherein the preadipocyte or white adipocyte is in a living subject.

7. The method of claim 6, wherein the living subject is an obese human subject.

8. A method of decreasing fat stores or weight in a subject, the method comprising identifying a subject in need of decreasing fat stores or weight, and administering to the subject a therapeutically effective amount of a small interfering RNA (siRNA) that binds specifically to an mRNA encoding Necdin, wherein the mRNA comprises SEQ ID NO:2, and wherein the siRNA selectively inhibits Necdin expression, in an amount sufficient to promote brown adipocyte differentiation in the subject, wherein the differentiation of brown adipocytes decreases fat stores or weight in the subject.

9. The method of claim 8, further comprising administering to the subject a second agent selected from the group consisting of bone morphogenetic protein 2 (BMP-2), bone morphogenetic protein 4 (BMP-4), bone morphogenetic protein 5 (BMP-5), bone morphogenetic protein 6 (BMP-6), or bone morphogenetic protein 7 (BMP-7), bone morphogenetic protein 1 (BMP-1), bone morphogenetic protein 3 (BMP-3), peroxisome proliferator-activated receptor gamma (PPARγ), Retinoid X receptor, alpha (RxRα), insulin, T3, a thiazolidinedione (TZD), vitamin A, retinoic acid, insulin, glucocorticoid or agonist thereof, Wnt, insulin-like growth factor (IGF), epidermal growth factor (EGF), fibroblast growth factor (FGF), transforming growth factor alpha (TGFα), transforming growth factor beta (TGFβ), tumor necrosis factor alpha (TNFα), Macrophage colony stimulating factor (MCSF), vascular endothelial growth factor (VEGF) and Platelet Derived Growth Factor (PDGF).

10. The method of claim 8, wherein the subject has type 2 diabetes.

11. The method of claim 1, further comprising implanting the differentiated brown adipocyte in a living subject.

12. The method of claim 11, wherein the subject is an obese subject.

13. The method of claim 7, wherein the subject has type 2 diabetes.

14. The method of claim 8, wherein the subject is an obese human subject.

15. The method of claim 1, wherein the siRNA comprises two strands, wherein the first strand comprises 16 or more nucleotides that are at least 95% identical to a target region in SEQ ID NO:2 and the second strand is complementary to the first strand.

16. The method of claim 8, wherein the siRNA comprises two strands, wherein the first strand comprises 16 or more nucleotides that are at least 95% identical to a target region in SEQ ID NO:2 and the second strand is complementary to the first strand.

17. The method of claim 1, further comprising contacting the preadipocyte or white adipocyte with bone morphogenetic protein 7 (BMP-7).

18. The method of claim 8, further comprising administering to the subject a therapeutically effective amount of bone morphogenetic protein 7 (BMP-7).

* * * * *

```
                             SEQUENCE LISTING

<160> NUMBER OF SEQ ID NOS: 37

<210> SEQ ID NO 1
<211> LENGTH: 321
<212> TYPE: PRT
<213> ORGANISM: Homo sapiens

<400> SEQUENCE: 1

Met Ser Glu Gln Ser Lys Asp Leu Ser Asp Pro Asn Phe Ala Ala Glu
1               5                   10                  15

Ala Pro Asn Ser Glu Val His Ser Ser Pro Gly Val Ser Glu Gly Val
                20                  25                  30

Pro Pro Ser Ala Thr Leu Ala Glu Pro Gln Ser Pro Pro Leu Gly Pro
            35                  40                  45

Thr Ala Ala Pro Gln Ala Ala Pro Pro Gln Ala Pro Asn Asp Glu
    50                  55                  60

Gly Asp Pro Lys Ala Leu Gln Gln Ala Ala Glu Glu Gly Arg Ala His
65                  70                  75                  80

Gln Ala Pro Ser Ala Ala Gln Pro Gly Pro Ala Pro Ala Pro Ala
                85                  90                  95

Gln Leu Val Gln Lys Ala His Glu Leu Met Trp Tyr Val Leu Val Lys
                100                 105                 110

Asp Gln Lys Lys Met Ile Ile Trp Phe Pro Asp Met Val Lys Asp Val
                115                 120                 125

Ile Gly Ser Tyr Lys Lys Trp Cys Arg Ser Ile Leu Arg Arg Thr Ser
    130                 135                 140

Leu Ile Leu Ala Arg Val Phe Gly Leu His Leu Arg Leu Thr Ser Leu
145                 150                 155                 160

His Thr Met Glu Phe Ala Leu Val Lys Ala Leu Glu Pro Glu Glu Leu
                165                 170                 175

Asp Arg Val Ala Leu Ser Asn Arg Met Pro Met Thr Gly Leu Leu Leu
                180                 185                 190

Met Ile Leu Ser Leu Ile Tyr Val Lys Gly Arg Gly Ala Arg Glu Ser
                195                 200                 205

Ala Val Trp Asn Val Leu Arg Ile Leu Gly Leu Arg Pro Trp Lys Lys
    210                 215                 220

His Ser Thr Phe Gly Asp Val Arg Lys Leu Ile Thr Glu Glu Phe Val
225                 230                 235                 240

Gln Met Asn Tyr Leu Lys Tyr Gln Arg Val Pro Tyr Val Glu Pro Pro
                245                 250                 255

Glu Tyr Glu Phe Phe Trp Gly Ser Arg Ala Ser Arg Glu Ile Thr Lys
                260                 265                 270

Met Gln Ile Met Glu Phe Leu Ala Arg Val Phe Lys Lys Asp Pro Gln
    275                 280                 285

Ala Trp Pro Ser Arg Tyr Arg Glu Ala Leu Glu Glu Ala Arg Ala Leu
                290                 295                 300

Arg Glu Ala Asn Pro Thr Ala His Tyr Pro Arg Ser Ser Val Ser Glu
305                 310                 315                 320

Asp
```

<210> SEQ ID NO 2
<211> LENGTH: 1460
<212> TYPE: DNA
<213> ORGANISM: Homo sapiens

<400> SEQUENCE: 2

| | | | | | |
|---|---|---|---|---|---|
| aagcttaaga | gtcctgttgg | agggactggt | gtggtaatgg | ctctgccaaa | agtgttatgt | 60 |
| gcgtgcaaac | ccaaagagag | aaagcacaga | aaacctttca | acatcaacct | gcttgaggaa | 120 |
| aaataaagtg | ggaaaagata | catactcaca | gtgaggactc | tagacatgtc | aagacaattt | 180 |
| ttaaatatgc | ttttggcttc | gagtggcaat | aactagattc | aagacagcat | atttaagaag | 240 |
| ctgctgatga | agaaaaccc | gggaagagct | gaaggaccac | atcagcccag | accaaggatg | 300 |
| ctgaagcagc | attaaggtcc | ctggtttcag | atgctcaggc | aatgacccct | tttttcatgg | 360 |
| agagcctgta | ggagtgacag | ttttgtcttt | gcccactggg | aatctgtttt | ccatacctgg | 420 |
| aaaacagggt | tacctatgtt | tcccctgcta | ccctttggtc | atctcagaga | cactaccaga | 480 |
| tattacccat | gggacctatt | tttttttaa | atctcaggaa | agacttgggt | gtggcttcca | 540 |
| acgtggagga | ctcagtagct | tcagagaggg | tcctgagaga | aggtgaattg | aagaatgagg | 600 |
| gtgctgggca | agggaaaag | acattatcat | gcaagtttgt | gctaaaagat | atagcaatcc | 660 |
| ttctgctatg | gactaagtat | ggaaaaaaat | aaaatggaat | caaagttacc | caaaggaatt | 720 |
| gtaaaaccca | atttatgccc | gttaaagcat | taatgatgct | ctaagtccac | tgcctactta | 780 |
| aaaagttcat | agttcacatg | ggtttgatag | gaaattacgt | ttaacgacac | actgcatttc | 840 |
| ccctttcttt | atagcctatc | tgatttggta | gggagtcgat | cattttttat | tggaatttct | 900 |
| caggattcca | acctcagaca | tccactttac | agtttacaca | tttcttgga | caagcccgac | 960 |
| tgttcctctc | actggttcgc | ataaagctca | tgtttacaaa | gccgcccaga | cctttctctg | 1020 |
| ggactctcat | atttaactta | attctggata | tacccaggta | agcgtttccc | aagaaacttg | 1080 |
| accccaacat | cccaaaaact | taaggtatct | ttcccttaaa | ctggccccct | tccagtacg | 1140 |
| catccatctc | acttctctcc | tgccctagat | cttctcagcc | caaacaggaa | accccgggat | 1200 |
| cgctctccca | gcaggtgaag | cctcgccatg | gaccctcccc | gtcggggccc | cgcgctgccc | 1260 |
| cgcccgcccc | cagccgctgg | ccaaggccgc | ggtcgcgcag | gcgcagtgcc | gcgtcccgcc | 1320 |
| gccgccccgc | cctgcccgtc | gctgcggaag | gcgccgcgcg | cagcaacgcg | cacttcctct | 1380 |
| ccaggaatcc | gcggagggag | cgcaggctcg | aagagctcct | ggacgcagag | gccctgccct | 1440 |
| tgccagacgg | cgcagacatg | | | | | 1460 |

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
gagtttgccc tggtcaaagc          20

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide -continued

```
<400> SEQUENCE: 4
catgggcata cggttgttga g                                              21

<210> SEQ ID NO 5
<211> LENGTH: 26
<212> TYPE: DNA
<213> ORGANISM: Artificial Sequence
<220> FEATURE:
<223> OTHER INFORMATION: Oligonucleotide

<400> SEQUENCE: 5
caccctgtct agctcctctg ggctga                                         26

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
cttatcaagc ccaagcgaag                                                20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide

<400> SEQUENCE: 7
cagggatgac atgtgtctgg                                                20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide

<400> SEQUENCE: 8
tcagctctgt ggacctctcc                                                20

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide

<400> SEQUENCE: 9
acccttgcat ccttcacaag                                                20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide

<400> SEQUENCE: 10
aggacaacga cctctgcatc                                                20

<210> SEQ ID NO 11
<211> LENGTH: 22
```

```
<212> TYPE: DNA
<213> ORGANISM: Artificial Sequence
<220> FEATURE:
<223> OTHER INFORMATION: Oligonucleotide

<400> SEQUENCE: 11
gtacgttatc tccttcactt tg                                              22

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide

<400> SEQUENCE: 12
agtacgaatg ctcctgcaca c                                               21

<210> SEQ ID NO 13
<211> LENGTH: 18
<212> TYPE: DNA
<213> ORGANISM: Artificial Sequence
<220> FEATURE:
<223> OTHER INFORMATION: Oligonucleotide

<400> SEQUENCE: 13
ctggccctca tcatccac                                                   18

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide

<400> SEQUENCE: 14
gtcaacagca aaagccacaa                                                 20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide

<400> SEQUENCE: 15
tctggggtca gaggaagaga                                                 20

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide

<400> SEQUENCE: 16
agacctattg agtggcgtga a                                               21

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide

<400> SEQUENCE: 17
```

-continued tgttggagat ggggaagaag                               20

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide

<400> SEQUENCE: 18
cttttggaac gagagcaagg                               20

<210> SEQ ID NO 19
<211> LENGTH: 22
<212> TYPE: DNA
<213> ORGANISM: Artificial Sequence
<220> FEATURE:
<223> OTHER INFORMATION: Oligonucleotide

<400> SEQUENCE: 19
aaagatataa aggagccgag ag                            22

<210> SEQ ID NO 20
<211> LENGTH: 19
<212> TYPE: DNA
<213> ORGANISM: Artificial Sequence
<220> FEATURE:
<223> OTHER INFORMATION: Oligonucleotide

<400> SEQUENCE: 20
aggacaagga atgggagga                                19

<210> SEQ ID NO 21
<211> LENGTH: 21
<212> TYPE: DNA
<213> ORGANISM: Artificial Sequence
<220> FEATURE:
<223> OTHER INFORMATION: Oligonucleotide

<400> SEQUENCE: 21
gtgttgtggg tatctcgaag g                             21

<210> SEQ ID NO 22
<211> LENGTH: 18
<212> TYPE: DNA
<213> ORGANISM: Artificial Sequence
<220> FEATURE:
<223> OTHER INFORMATION: Oligonucleotide

<400> SEQUENCE: 22
cacccggcca tacttcct                                 18

<210> SEQ ID NO 23
<211> LENGTH: 19
<212> TYPE: DNA
<213> ORGANISM: Artificial Sequence
<220> FEATURE:
<223> OTHER INFORMATION: Oligonucleotide

<400> SEQUENCE: 23
cacttacgcc gcatgttct                                19

<210> SEQ ID NO 24
<211> LENGTH: 18
<212> TYPE: DNA
<213> ORGANISM: Artificial Sequence

```
<220> FEATURE:
<223> OTHER INFORMATION: Oligonucleotide

<400> SEQUENCE: 24
gctgctgctg ctcttgtg                                                   18

<210> SEQ ID NO 25
<211> LENGTH: 18
<212> TYPE: DNA
<213> ORGANISM: Artificial Sequence
<220> FEATURE:
<223> OTHER INFORMATION: Oligonucleotide

<400> SEQUENCE: 25
tcggaaacgg aactggaa                                                   18

<210> SEQ ID NO 26
<211> LENGTH: 25
<212> TYPE: DNA
<213> ORGANISM: Artificial Sequence
<220> FEATURE:
<223> OTHER INFORMATION: Oligonucleotide

<400> SEQUENCE: 26
ggttgttata gaagctaatt cttgg                                           25

<210> SEQ ID NO 27
<211> LENGTH: 20
<212> TYPE: DNA
<213> ORGANISM: Artificial Sequence
<220> FEATURE:
<223> OTHER INFORMATION: Oligonucleotide

<400> SEQUENCE: 27
gcattccttg atgcctgtct                                                 20

<210> SEQ ID NO 28
<211> LENGTH: 20
<212> TYPE: DNA
<213> ORGANISM: Artificial Sequence
<220> FEATURE:
<223> OTHER INFORMATION: Oligonucleotide

<400> SEQUENCE: 28
ctcctctcta cccectgtcc                                                 20

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide

<400> SEQUENCE: 29
ttgggttctg cctgtgtttt                                                 20

<210> SEQ ID NO 30
<211> LENGTH: 19
<212> TYPE: DNA
<213> ORGANISM: Artificial Sequence
<220> FEATURE:
<223> OTHER INFORMATION: Oligonucleotide

<400> SEQUENCE: 30
cgtggagcaa cggtatgag                                                  19
```

-continued

<210> SEQ ID NO 31
<211> LENGTH: 21
<212> TYPE: DNA
<213> ORGANISM: Artificial Sequence
<220> FEATURE:
<223> OTHER INFORMATION: Oligonucleotide

<400> SEQUENCE: 31
tccctgcctt gatgtgtagt t                                      21

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide

<400> SEQUENCE: 32
attaagaagg ggctggagga                                        20

<210> SEQ ID NO 33
<211> LENGTH: 19
<212> TYPE: DNA
<213> ORGANISM: Artificial Sequence
<220> FEATURE:
<223> OTHER INFORMATION: Oligonucleotide

<400> SEQUENCE: 33
aggtggtcag gtgtgatgg                                         19

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide

<400> SEQUENCE: 34
aatgtgtgat gcctttgtgg                                        20

<210> SEQ ID NO 35
<211> LENGTH: 18
<212> TYPE: DNA
<213> ORGANISM: Artificial Sequence
<220> FEATURE:
<223> OTHER INFORMATION: Oligonucleotide

<400> SEQUENCE: 35
acgcccagtt tgaaggaa                                          18

<210> SEQ ID NO 36
<211> LENGTH: 57
<212> TYPE: DNA
<213> ORGANISM: Artificial Sequence
<220> FEATURE:
<223> OTHER INFORMATION: Oligonucleotide

<400> SEQUENCE: 36
tcgaggagta tcccaaatgg acagttcaag agactgtcca tttgggatac tcttttt    57

<210> SEQ ID NO 37
<211> LENGTH: 57
<212> TYPE: DNA
<213> ORGANISM: Artificial Sequence
<220> FEATURE:
<223> OTHER INFORMATION: Oligonucleotide

```
<400> SEQUENCE: 37
ctagaaaaag agtatcccaa atggacagtc tcttgaactg tccatttggg atactcc        57
```